US00RE42903E

(19) United States
(12) Reissued Patent
Deffenbaugh et al.

(10) Patent Number: US RE42,903 E
(45) Date of Reissued Patent: Nov. 8, 2011

(54) ELECTRONICALLY CONTROLLED PROSTHETIC KNEE

(75) Inventors: Bruce W. Deffenbaugh, Honolulu, HI (US); Hugh M. Herr, Somerville, MA (US); Gill A. Pratt, Lexington, MA (US); Michael B. Wittig, Fremont, CA (US)

(73) Assignee: Massachusetts Institute of Technology, Cambridge, MA (US)

(21) Appl. No.: 11/490,508

(22) Filed: Jul. 20, 2006

Related U.S. Patent Documents

Reissue of:
(64) Patent No.: 6,764,520
Issued: Jul. 20, 2004
Appl. No.: 09/767,367
Filed: Jan. 22, 2001

U.S. Applications:
(60) Provisional application No. 60/177,108, filed on Jan. 20, 2000.

(51) Int. Cl.
*A61F 2/48* (2006.01)

(52) U.S. Cl. ..... 623/24; 623/26; 623/39

(58) Field of Classification Search ..... 623/24–27, 623/39–45, 47–56
See application file for complete search history.

(56) References Cited

U.S. PATENT DOCUMENTS

| | | | |
|---|---|---|---|
| 4,005,496 | A | 2/1977 | Wilkes |
| 4,064,569 | A | 12/1977 | Campbell |
| 4,200,003 | A | 4/1980 | Miller |
| 4,685,927 | A | 8/1987 | Haupt |
| 4,790,522 | A | 12/1988 | Drutchas |
| 4,795,474 | A | 1/1989 | Horvath |
| 4,854,428 | A | 8/1989 | Horvath |
| 4,893,648 | A | 1/1990 | Horvath |
| 4,958,705 | A | 9/1990 | Horvath |
| 5,092,902 | A | 3/1992 | Adams et al. |
| 5,181,931 | A | 1/1993 | van de Veen |
| 5,277,281 | A | 1/1994 | Carlson et al. |

(Continued)

FOREIGN PATENT DOCUMENTS

DE 43 05 213 A1 8/1993

(Continued)

OTHER PUBLICATIONS

Ari Wilkenfeld & Hugh Herr, *An Auto-Adaptive External Knee Prosthesis,* Artificial Intelligence Laboratory, MIT, Cambridge, Massachusetts, Sep. 2000, 3 pages.

(Continued)

*Primary Examiner* — Alvin J Stewart
(74) *Attorney, Agent, or Firm* — Knobbe Martens Olson & Bear, LLP

(57) ABSTRACT

The present invention relates to a variable-torque magnetorheologically actuated prosthetic knee which utilizes a plurality of interspersed and alternating rotors and stators to shear magnetorheological fluid in gaps formed therebetween. Advantageously, by operating in the "shear mode" there is substantially no or negligible fluid pressure buildup or change. Moreover, the multiple MR fluid gaps or flux interfaces desirably allow for the production of a large torque at low speed—eliminating the need for a transmission—and also for a wide dynamic torque range. One embodiment of the invention allows the rotors and/or stators to close the gaps therebetween to create a frictional torque component, thereby forming a "hybrid" braking system which provides a total torque or damping which is a combination of viscous torque and frictional torque.

64 Claims, 22 Drawing Sheets

U.S. PATENT DOCUMENTS

| | | | | |
|---|---|---|---|---|
| 5,284,330 | A | | 2/1994 | Carlson et al. |
| 5,376,137 | A | | 12/1994 | Shorter et al. |
| 5,383,939 | A | | 1/1995 | James |
| 5,443,521 | A | | 8/1995 | Knoth et al. |
| 5,472,412 | A | | 12/1995 | Knoth |
| 5,476,441 | A | | 12/1995 | Durfee et al. |
| 5,545,232 | A | | 8/1996 | van de Veen |
| 5,545,233 | A | | 8/1996 | Fitzlaff |
| 5,571,205 | A | | 11/1996 | James |
| 5,632,725 | A | | 5/1997 | Silver et al. |
| 5,645,590 | A | | 7/1997 | van de Veen |
| 5,645,752 | A | | 7/1997 | Weiss et al. |
| 5,670,077 | A | | 9/1997 | Carlson et al. |
| 5,683,615 | A | | 11/1997 | Munoz |
| 5,704,945 | A | | 1/1998 | Wagner et al. |
| 5,711,746 | A | | 1/1998 | Carlson |
| 5,728,174 | A | | 3/1998 | Fitzlaff |
| 5,746,774 | A | | 5/1998 | Kramer et al. |
| 5,749,533 | A | | 5/1998 | Daniels |
| 5,755,813 | A | | 5/1998 | Krukenberg |
| 5,823,309 | A | | 10/1998 | Gopalswamy et al. |
| 5,842,547 | A | | 12/1998 | Carlson et al. |
| 5,888,212 | A | | 3/1999 | Petrofsky et al. |
| 5,888,236 | A | | 3/1999 | van de Veen |
| 5,893,891 | A | | 4/1999 | Zahedi |
| 5,900,184 | A | | 5/1999 | Weiss et al. |
| 5,906,767 | A | | 5/1999 | Karol et al. |
| 5,941,913 | A | | 8/1999 | Woolnough et al. |
| 5,947,238 | A | | 9/1999 | Jolly et al. |
| 5,948,021 | A | | 9/1999 | Radcliffe |
| 5,960,918 | A | | 10/1999 | Moser et al. |
| 5,967,273 | A | | 10/1999 | Hampton |
| 5,972,035 | A | | 10/1999 | Blatchford |
| RE36,521 | E | | 1/2000 | Hiemisch |
| 6,027,664 | A | | 2/2000 | Weiss et al. |
| 6,095,486 | A | | 8/2000 | Ivers et al. |
| 6,113,642 | A | * | 9/2000 | Petrofsky et al. ..... 623/24 |
| 6,139,586 | A | | 10/2000 | Wagner et al. |
| 6,165,226 | A | | 12/2000 | Wagner |
| 6,168,634 | B1 | | 1/2001 | Schmitz |
| 6,187,051 | B1 | | 2/2001 | Gerad van de Veen |
| 6,206,933 | B1 | | 3/2001 | Shorter et al. |
| 6,241,775 | B1 | | 6/2001 | Blatchford |
| 6,352,144 | B1 | | 3/2002 | Brooks |
| 6,423,098 | B1 | | 7/2002 | Biedermann |
| 6,443,993 | B1 | | 9/2002 | Koniuk |
| 6,517,585 | B1 | | 2/2003 | Zahedi et al. |
| 6,679,920 | B2 | | 1/2004 | Biedermann et al. |
| 6,719,806 | B1 | | 4/2004 | Zahedi et al. |
| 6,755,870 | B1 | | 6/2004 | Biedermann et al. |

FOREIGN PATENT DOCUMENTS

| | | | |
|---|---|---|---|
| DE | 43 18 901 | A1 | 1/1994 |
| DE | 195 21 464 | A1 | 3/1997 |
| EP | 0 503 775 | A1 | 9/1992 |
| EP | 0 628 296 | A2 | 12/1994 |
| EP | 0 654 254 | B1 | 9/1999 |
| EP | 0 957 838 | B1 | 8/2000 |
| EP | 1 125 825 | A2 | 8/2001 |
| FR | 2 623 086 | A1 | 5/1989 |
| GB | 2 244 006 | A | 11/1991 |
| GB | 2 328 160 | A | 2/1999 |
| GB | 2 334 891 | A | 9/1999 |
| GB | 2 338 653 | A | 12/1999 |
| JP | 60-81530 | A | 5/1985 |
| JP | S60-81530 | A | 5/1985 |
| JP | 01-158233 | | 6/1989 |
| JP | 02-150516 | | 6/1990 |
| WO | WO 94/06374 | A1 | 3/1994 |
| WO | WO 95/26171 | A1 | 10/1995 |
| WO | WO 96/41599 | A1 | 12/1996 |
| WO | WO 98/38951 | A1 | 9/1998 |
| WO | WO 99/08621 | A2 | 2/1999 |
| WO | WO 99/29272 | | 6/1999 |
| WO | WO 99/29272 | A1 | 6/1999 |
| WO | WO 99/44547 | A1 | 9/1999 |
| WO | WO 00/38599 | A1 | 7/2000 |
| WO | WO 01/17466 | A2 | 3/2001 |

OTHER PUBLICATIONS

Ari Wilkenfeld, Ph.D., *Biologically inspired autoadaptive control of a knee prosthesis,* Dissertation Abstract, MIT, Cambridge, Massachusetts, Sep. 2000, 1 page.

Otto Bock Orthopadische Industrie, *C-LEG A New Dimension in Amputee Mobility,* 1997, 4 pages.

*State-Of-The-Art Prosthetic Leg Incorporates Magneto-Rheological Technology,* Medical Product Manufacturing News, Nov. 2000, p. 42.

Ari J. Wilkenfeld, *Biologically Inspired Autoadaptive Control of a Knee Prosthesis,* Ph.D. Dissertation, Massachusetts Institute of Technology, 2000, 106 pages.

Office Action in corresponding Japanese Patent Application No. 2001-555610, dated May 21, 2008, with English translation, 8 pp.

Office Action in corresponding Japanese Patent Application No. 2001-555610, dated Feb. 4, 2009, 11 pp.

* cited by examiner

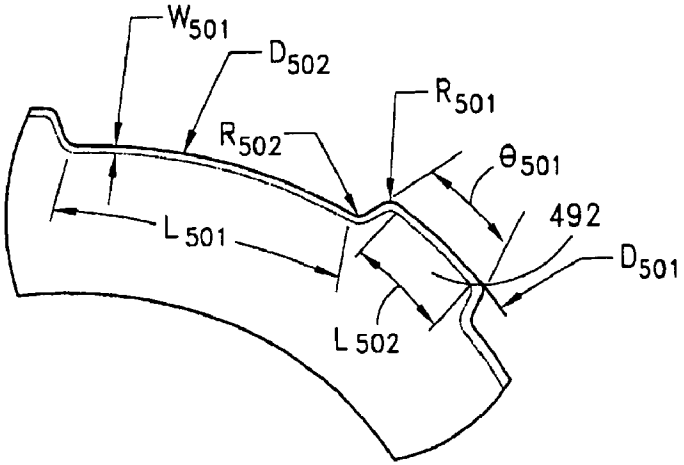
FIG. 50
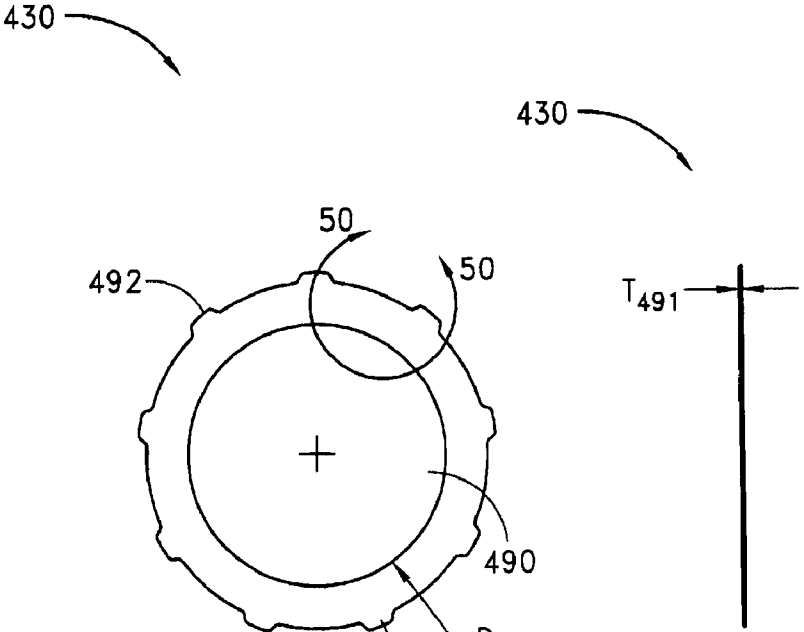
FIG. 49
FIG. 48

ELECTRONICALLY CONTROLLED PROSTHETIC KNEE

Matter enclosed in heavy brackets [ ] appears in the original patent but forms no part of this reissue specification; matter printed in italics indicates the additions made by reissue.

RELATED APPLICATIONS

This application claims the benefit of U.S. Provisional application No. 60/177,108, filed Jan. 20, 2000, the entire disclosure of which is hereby incorporated by reference herein.

BACKGROUND OF THE INVENTION

1. Field of the Invention

The present invention relates to prosthetic joints in general and, in particular, to controllable braking systems for prosthetic knee joints.

2. Description of the Related Art

Three types of variable-torque brakes have been employed in prosthetic knees in the past: (i) dry friction brakes where one material surface rubs against another surface with variable force; (ii) viscous torque brakes using hydraulic fluid squeezed through a variable sized orifice or flow restriction plate; and (iii) magnetorheological (MR) brakes or dampers where MR fluid (containing small iron particles suspended in the fluid) is squeezed through a fixed orifice or flow restriction plate, with viscosity of the fluid being varied in response to an applied magnetic field. Each of these technologies, as conventionally practiced in the field of prosthetics, can pose certain disadvantages.

Though dry friction brakes can generally provide a substantial torque range for their size, undesirably, they are often difficult to control. After extended use, the frictional pads tend to wear, thereby changing the frictional characteristics of the brake and the torque response for a given commanded torque. Disadvantageously, this can cause unreliable damping performance, and hence adversely affect the gait of the amputee and also cause discomfort to the amputee. Consequently, dry friction brakes may need frequent servicing and/or replacement which undesirably adds to the cost.

Under high loading conditions, viscous torque brakes are susceptible to leakage of hydraulic fluid and possibly other damage due to excessive pressure build-up. Disadvantageously, this can result in an irreversible state, since once the brake unit is overloaded it cannot return to normal. Therefore, such a viscous torque brake for a prosthetic joint is prone to catastrophic failure, and hence can be unreliable and detrimental to the safety of an amputee.

The term "valve mode" refers to the control of the flow of a MR fluid through an orifice by the application of a variable magnetic field perpendicular to the direction of the flow in place of the mechanical valve used in conventional viscous torque brakes. Disadvantageously, a MR brake operated in the "valve mode" also develops internal fluid pressure buildup, and hence is still susceptible to traditional pressure-induced failure, thereby putting the amputee at risk.

SUMMARY OF THE INVENTION

Accordingly it is one important advantage of the present invention to overcome some or all of the above limitations by providing a variable-torque magnetorheologically actuated prosthetic knee which utilizes a plurality of interspersed and alternating rotors and stators to shear magnetorheological fluid in gaps formed therebetween. Advantageously, by operating in the "shear mode" there is substantially no or negligible fluid pressure buildup or change. Moreover, the multiple MR fluid gaps or flux interfaces desirably allow for the production of a large torque at low speed—eliminating the need for a transmission—and also for a wide dynamic torque range. One embodiment of the invention allows the rotors and/or stators to close the gaps therebetween to create a frictional torque component, thereby forming a "hybrid" braking system which provides a total torque or damping which is a combination of viscous torque and frictional torque.

In accordance with one preferred embodiment, a magnetorheologically actuated rotary prosthetic knee is provided for precisely and rapidly controlling lower limb movement. The prosthetic knee generally comprises a substantially central core and a pair of side plates, a plurality of interspersed and alternating magnetically soft rotors and magnetically soft stators, an electromagnet positioned between the core and the rotors and stators, and a pair of bearings. The core and the side plates are formed from a magnetically soft material to create a magnetic return path. The rotors and stators are arranged so as to form a plurality of gaps therebetween. The gaps contain a magnetorheological fluid which is sheared during knee rotation. The electromagnet is responsive to an electrical signal to generate a variable magnetic field to cause a controlled change in the viscosity of the magnetorheological fluid. The bearings are in rotary communication with the rotors and a shin portion of the lower limb to transfer rotary resistive torques from the prosthetic knee to the shin portion.

In accordance with another preferred embodiment, a controllable magnetorheological brake for an artificial knee is provided to dampen knee joint rotation. The magnetorheological knee generally comprises a plurality of alternatingly arranged and spaced magnetizable rotors and magnetizable stators, a magnetorheological fluid, and a magnet. The rotors and stators are concentrically configured about a longitudinal axis of rotation of the artificial knee. The magnetorheological fluid resides in a plurality of gaps formed between the rotors and the stators. The magnet is responsive to an applied voltage and adapted to generate a variable magnetic field which passes through the rotors, the stators and the magnetorheological fluid. The shearing of the magnetorheological fluid in the gaps between the rotors and the stators creates a variable torque output which precisely controls the rotation of the artificial knee.

In accordance with yet another preferred embodiment, an electronically controlled prosthetic knee is provided for generating a wide dynamic torque range. The prosthetic knee generally comprises a plurality of rotors, a plurality of stators, and a fluid adapted to undergo a rheology change in response to an applied magnetic field. The rotors comprise a ferrous material. The rotors are rotatable and laterally displaceable about a longitudinal axis of rotation of the prosthetic knee. The stators comprise a ferrous material and are alternatingly interspersed with the rotors to form gaps therebetween. The stators are laterally displaceable about the axis of rotation of the prosthetic knee. The fluid resides in the gaps formed between the rotors and the stators. Actuation of the magnetic field generates during knee rotation a controllable variable knee damping torque.

In accordance with a further preferred embodiment, a rotary prosthetic knee for an amputee is provided. The prosthetic knee generally comprises a rotatable inner spline, a plurality of rotors engaged with the inner spline, a plurality of stators alternatingly interspersed with the rotors, an outer spline engaged with the stators, and a magnetically controlled medium residing in a plurality of sealed gaps between the rotors and the stators. The magnetically controlled medium is adapted to undergo a controlled bulk property change in response to an applied magnetic field such that the rotation of the rotors which shear the magnetically controlled medium is precisely controlled and the rotation of the prosthetic knee is variably damped to provide a substantially natural gait for the amputee.

In accordance with one preferred embodiment, a variable torque magnetorheological brake for a prosthetic knee is provided. The brake generally comprises a substantially central core, a first side plate connected to a first end of the core, a second side plate connected to a second end of the core and a rotatable and laterally displaceable blade positioned between the first side plate and the second side plate. The brake further comprises magnetorheological fluid in a pair of microgaps formed between the blade and the plates, and a magnet to generate a magnetic field such that a magnetic circuit is created through the core, the first side plate, the second side plate, the blade and the magnetorheological fluid. The microgaps have a size which is optimally minimized such that when the magnetic field has a zero value there is substantially no frictional contact between the blade and the side plates, thereby allowing the prosthetic knee to swing freely and provide a wide dynamic range.

In accordance with another preferred embodiment, a controllable rotary damper for an artificial knee is provided. The damper generally comprises a plurality of interspersed inner rotors and outer rotors, a plurality of magnetorheological fluid films, a pair of side plates and an electromagnet. The inner rotors and outer rotors are concentrically arranged about a longitudinal axis of the artificial knee. The magnetorheological fluid films are resident in a plurality of gaps between the inner rotors and the outer rotors. The pair of side plates sandwiches the inner rotors and the outer rotors with at least one of the side plates being laterally movable along the longitudinal axis of the artificial knee. The electromagnet is adapted to create a magnetic field through the inner rotors, the outer rotors, the magnetorheological fluid and the side plates. The relative rotation between the inner rotors and the outer rotors and the lateral movement of at least one of the side plates generates a variable damping torque to control the rotation of the artificial knee.

In accordance with one preferred embodiment, a prosthetic knee is provided. The prosthetic knee generally comprises a plurality of rotors, a plurality of stators and a fluid adapted to undergo a rheology change in response to an applied magnetic field. The rotors are rotatable about a longitudinal axis of the prosthetic knee. The stators are [alternating] *alternatingly* interspersed with the rotors to form gaps therebetween. The fluid resides in the gaps formed between the rotors and the stators. Controlled variation of the magnetic field varies the fluid rheology and shearing of the fluid caused by relative rotation between the rotors and stators during knee rotation generates a controllable variable knee torque.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which:

FIG. 48 is a front view of a stator having features and advantages in accordance with one preferred embodiment of the present invention;

FIG. 49 is a side view of the stator of FIG. 48;

FIG. 50 is an enlarged view of region 50-50 of FIG. 48; and

DETAILED DESCRIPTION OF THE PREFERRED EMBODIMENTS

Understanding normal human walking/running provides the basis for the design and development of effective lower limb prostheses with controlled motion. Normal human locomotion or gait can be described as a series of rhythmical alternating movements of the limbs and trunk which result in the forward progression of the body's center of gravity.

Figure 1:
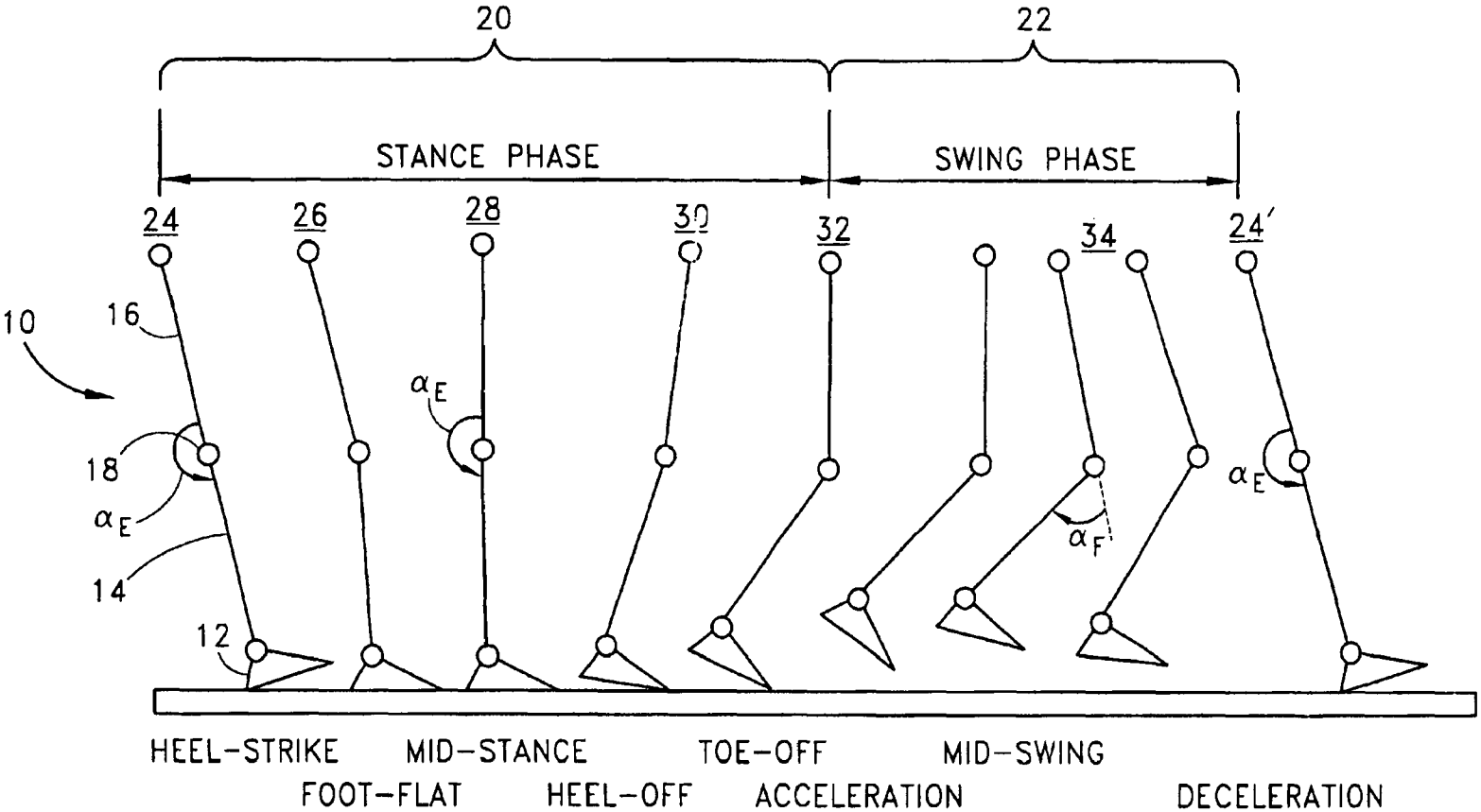
FIG. 1 is a schematic drawing of one normal human locomotion cycle illustrating the various limb positions during stance and swing phases.

One typical gait cycle, as schematically depicted in FIG. 1, comprises of the activity that occurs between heel strike of one lower limb 10 and the subsequent heel strike of the same limb 10. The limb or leg 10 generally comprises a foot 12 and a shin portion 14 coupled or articulated to a thigh portion 16 via a knee or knee joint 18. During a single gait cycle each lower limb or extremity passes through one stance or extended phase 20 and one swing phase 22.

The stance phase 20 begins at heel-strike 24 when the heel touches the floor or supporting ground surface and the stance knee begins to flex slightly. This flexion allows for shock absorption upon impact and also maintains the body's center of gravity at a more constant vertical level during stance.

Shortly after heel-strike 24, the sole makes contact with the ground at the beginning of the foot-flat phase 26. After maximum flexion is reached in the stance knee, the joint begins to extend again, until maximum extension is reached at [mid-stance] *mid-stance* 28 as the body weight is swung directly over the supporting extremity and continues to rotate over the foot.

As the body mass above the ankle continues to rotate forward, the heel lifts off the ground at heel-off 30. Shortly after this, the body is propelled forward by the forceful action of the calf-muscles (push-off). The push-off phase terminates when the entire foot rises from the ground at toe-off 32.

During late stance, the knee of the supporting leg flexes in preparation for the foot leaving the ground for swing. This is typically referred to in the literature as "knee break". At this time, the adjacent foot strikes the ground and the body is in "double support mode", that is, both the legs are supporting the body weight.

At toe-off 32, as the hip is flexed and the knee reaches a certain angle at knee break, the foot leaves the ground and the knee continues to flex into the swing phase. During early swing the foot accelerates. After reaching maximum flexion at mid-swing 34, the knee begins to extend and the foot decelerates. After the knee has reached full extension, the foot once again is placed on the ground at heel-strike 24' and the next walking cycle begins.

Typically, the anatomical position is the upright position, therefore flexion is a movement of a body part away from the extended or stance or anatomical position. Thus, bending of the knee is knee flexion. Extension is a movement of a limb towards the anatomical position, thus knee extension is a movement in the "straightening" direction.

During a typical normal walking progression on a generally level surface, the maximum flexion angle $\alpha_F$ varies between about 70° and 80°. The maximum extension angle $\alpha_E$ is typically about or close to 180°. Thus, in level walking the normal human knee rotates through a range of approximately 70°-80° going from a position of full extension in early and mid stance to 70°-80° of flexion shortly after toe-off. In other situations, for example, in a sitting position, the maximum flexion angle $\alpha_F$ can be about 140°-150°.

System Overview

Figure 2:
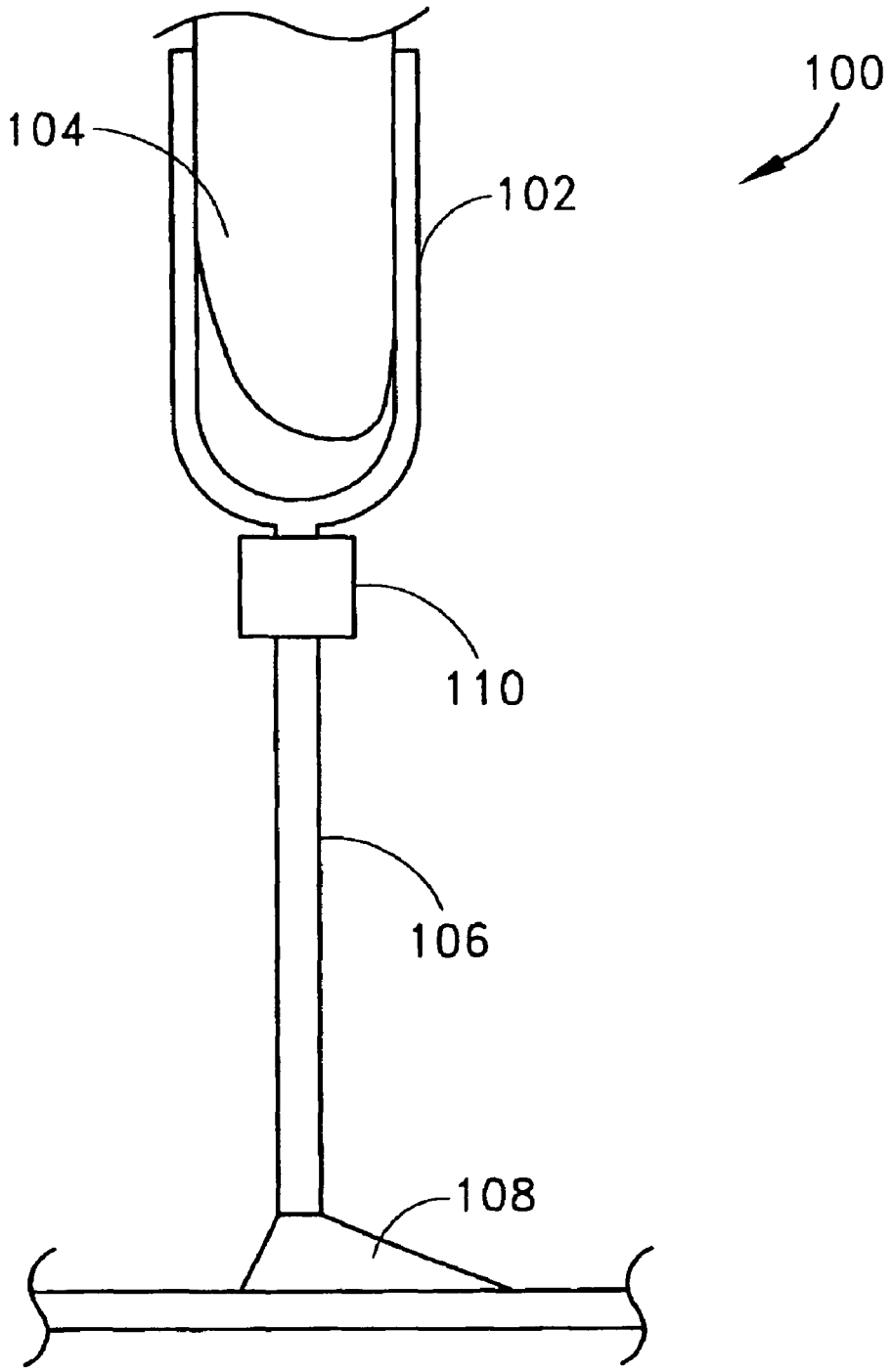
FIG. 2 is a schematic illustration of a lower limb prosthetic assembly comprising an electronically controlled prosthetic knee and having features and advantages in accordance with one preferred embodiment of the present invention.

FIG. 2 is a schematic illustration of a lower limb prosthetic assembly or prosthesis 100 comprising an electronically controlled active knee prosthesis and-having features and advantages in accordance with one preferred embodiment of the present invention. As described in greater detail later herein, preferably, the active knee prosthesis comprises a variable-torque magnetorheological (MR) braking system 110 for providing resistive forces to substantially simulate the position and motion of a natural knee joint during ambulation and/or other locomotory activities performed by the amputee. At one end the artificial knee 110 is coupled or mechanically connected to a residual limb socket 102 which receives a residual limb or femur portion 104 of the amputee while the other end of the prosthetic knee 110 is coupled or mechanically connected to a pylon or shank portion 106 which in turn is coupled or mechanically connected to a prosthetic or artificial foot 108.

Advantageously, the prosthetic knee joint 110 of the present invention permits the amputee to move and/or adapt comfortably and safely in a wide variety of circumstances. For example, during walking, running, sitting down, or when encountering subtle or drastic changes in the environment or ambient conditions, such as, when the user lifts a suitcase or walks down a slope.

The artificial knee joint 110 provides stance control to limit buckling when weight is applied to the limb. In addition, the prosthetic knee 110 provides aerial swing control so that the knee reaches full extension just prior to or at heel-strike in a smooth and natural manner. Moreover, the prosthetic knee 110, by adjusting and/or fine tuning the range and/or magnitudes of the resistive torque level, can be adapted for use with a wide variety of patients having different body weights, heights and activity levels.

Preferably, the artificial knee joint 110 of the present invention is used in conjunction with a trans-femoral (above-knee, A/N) amputee. Alternatively or optionally, the prosthetic knee joint 110 may be adapted for use with a knee-disarticulation (K/D) amputee where the amputation is through the knee joint, as needed or desired, giving due consideration to the goals of providing a substantially natural feeling and/or safe prosthetic device, and/or of achieving one or more of the benefits and advantages as taught or suggested herein.

Figure 3:
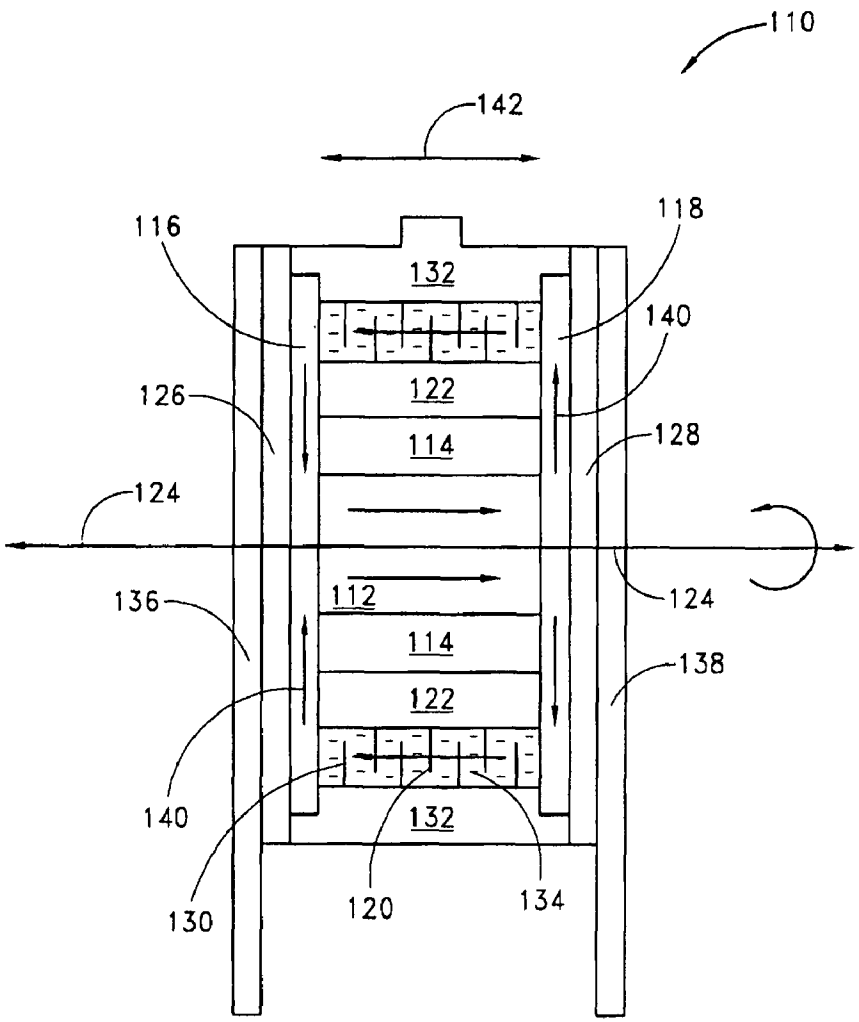
FIG. 3 is a simplified schematic drawing illustrating the general overall configuration of one preferred embodiment of the prosthetic knee of the present invention.

FIG. 3 is a simplified schematic of a rotary prosthetic knee or magnetorheological (MR) braking system 110 in accordance with one preferred embodiment of the present invention. The knee actuator 110 includes a substantially central core 112 substantially circumscribed or enveloped by an electromagnet or magnetic coil 114 and in mechanical communication with a pair of side plates or disks 116, 118. By passing a variable, controlled current through the electromagnet 114, a variable magnetic field is created. Preferably, the core 112 and side plates 116, 118 are fabricated from a ferrous, magnetizable or magnetic material and the like. More preferably, the core 112 and side plates 116, 118 are fabricated from a magnetically soft material of high flux saturation density and high magnetic permeability.

The prosthetic knee 110 further includes a plurality of inner blades or plates 120 in mechanical communication with an inner spline 122. The inner spline 122 generally circumscribes or envelops the electromagnet 114 and is coupled or mechanically connected to the side plates 116, 118. The blades 120 are preferably concentrically arranged about the brake axis of rotation 124. The inner spline 122 is preferably rotatable about the knee joint axis of rotation 124, and hence so are the blades or rotors 120 and the core side plates 116, 118. Rotation of the inner spline 122 corresponds to rotation or movement of the lower (below the knee) part of the leg.

The prosthetic knee 110 also comprises a plurality of outer blades or plates 130 in mechanical communication with an outer spline 132. The outer spline 132 generally circumscribes or envelops the inner spline 122. The blades 130 are preferably concentrically arranged about the brake axis of rotation 124. The outer spline 132 is preferably rotatable about the knee joint axis of rotation 124, and hence so are the blades or stators 130. Rotation of the outer spline 132 corresponds to rotation or movement of the upper (above the knee) part of the leg. Preferably, the outer spline or housing 132 comprises means to facilitate connection of the prosthetic knee joint 110 to a suitable stump socket or the like. The outer spline 132, and hence the stators 130, are preferably substantially irrotationally coupled to or nonrotatable with respect to the stump socket or residual limb.

The plurality of rotors 120 and stators 130 are interspersed in an alternating fashion and the gaps between adjacent blades 120 and 130 comprise a magnetorheological (MR) fluid 134, which thereby resides in the cavity or passage formed between the inner spline 122 and the outer spline 132. In one preferred embodiment, the MR fluid 134 in the gaps or micro-gaps between adjacent rotors 120 and stators 130 is in the form of thin lubricating films between adjacent rotors 120 and stators 130. Shearing of MR fluid present between the side plates 116, 118 and adjacent stators 130 can also contribute to the knee damping.

During knee joint rotation, the MR fluid in the plurality of gaps between the rotors 120 and stators 130 is sheared to generate a damping torque to control the limb rotation. The blades or disks 120 and 130 are preferably formed of a ferrous, magnetizable or magnetic material and the like. More preferably, the blades or disks 120 and 130 are formed of a material of as high magnetic permeability and magnetic softness as is mechanically practical.

The knee joint 110 further includes a pair of ball bearings 126, 128 coupled or connected to the respective side plates 116, 118. The ball bearings 126, 128 are further coupled or connected to respective side walls or mounting forks 136, 138. Thus, a rotary coupling is created between the inner spline 122 and the mounting forks 136, 138. The mounting forks 136, 138 in combination with the outer spline 132 form one main outer shell of the knee joint 110. Preferably, the side walls or mounting forks 136, 138 comprise means to facilitate connection of the prosthetic knee joint 110 to a suitable pylon, shank portion or the like, as described below.

Preferably, the central core 112 and the electromagnet 114 also rotate along with the rotation of the inner spline 122, the rotors 120, the core side plates 116, 118 and the mounting forks 136, 138. The stators 130 rotate together with the rotation of the outer spline 132.

The rotors 120 are rotationally fixed relative to the inner spline 122 and the stators 130 are rotationally fixed relative to the outer spline 132. During various stages of locomotion or knee rotation, and about the knee axis of rotation 124, the rotors 120 may rotate while the stators 130 are rotationally substantially stationary, or the stators 130 may rotate while the rotors 120 are rotationally substantially stationary, or both the rotors 120 and the stators 130 may rotate or be substantially rotationally stationary. The terms "rotor" and "stator" are used to distinguish the inner blades 120 and the outer blades 130, though both rotors 120 and stators 130 can rotate, and teach that relative rotational motion is created between the rotors 120 and the stators 130 (with MR fluid being sheared in the gaps between adjacent rotors 120 and stators 130). If desired, the blades 120 can be referred to as the "inner rotors" and the blades 130 as the "outer rotors."

Actuation of the magnet 114 causes a magnetic field, circuit or path 140 to be generated or created within the knee joint 110. In one preferred embodiment, the magnetic field 140 passes through the central core 112, radially outwards through the side plate 118, laterally through the interspersed set of rotors 120 and stators 130 and the magnetorheological fluid 134, and radially inwards through the side plate 116. The portion of the magnetic field 140 passing through the core 112 and side plates 116, 118 generally defines the magnetic return path while the active or functional magnetic field is generally defined by the magnetic path through the rotors 120, stators 130 and MR fluid 134.

The magnetorheological (MR) fluid 134 undergoes a rheology or viscosity change which is dependent on the magnitude of the applied magnetic field. In turn, this variation in fluid viscosity determines the magnitude of the shearing force/stress, torque or torsional resistance generated, and hence the level of damping provided by the prosthetic knee 110. Thus, by controlling the magnitude of this magnetic field, the rotary motion of the artificial limb is controlled, for example, to control the flexion and extension during swing and stance phases to provide a more natural and safe ambulation for the amputee.

In one preferred embodiment, the rotors 120 and/or stators 130 are displaceable in the lateral direction 142, and hence under the influence of a magnetic field can rub against adjacent rotors 120 and/or stators 130 with a variable force determined by the strength of the magnetic field to create a "hybrid" magnetorheological and frictional damping brake. In another preferred embodiment, the rotors 120 and stators 130 are laterally fixed in position relative to the splines 122 and 132, and hence the braking effect is substantially purely magnetorheological or viscous. Alternatively, some of the rotors 120 and/or stators 130 may be laterally fixed while others may be laterally displaceable, as required or desired, giving due consideration to the goals of providing a substantially natural feeling and/or safe prosthetic device, and/or of achieving one or more of the benefits and advantages as taught or suggested herein. In one embodiment, the side plates 116, 118 are laterally displaceable and contribute to the frictional damping due to frictional contact with adjacent stators 130.

Advantageously, by operating in the shear mode, there is no or negligible pressure build-up within the MR actuated prosthetic knee of the present invention. This substantially eliminates or reduces the chances of fluid leakage and failure of the knee, and hence desirably adds to the safety of the device.

Also advantageously, the multiple shearing surfaces or flux interfaces, provided by the preferred embodiments of the present invention, behave like a torque multiplier and allow the viscous torque level to be stepped up to a desired maximum value without the use of an additional transmission or other auxiliary component. For example, if two flux interfaces can provide a maximum viscous torque of about 1 N/m, then forty flux interfaces will be able to provide a viscous damping torque of about 40 N/m. In contrast, if a 40:1 step-up transmission is used to increase the viscous torque, disadvantageously, not only is the system reflected inertia magnified by a factor of about 1600, but the system weight, size and complexity are undesirably increased.

The multiple shearing surfaces or interfaces of the prosthetic knee of the preferred embodiments also advantageously allow for a wide dynamic torque range to be achieved which permits safe and/or more natural ambulation for the patient. Desirably, the MR actuated prosthetic knee of the preferred embodiments provides a rapid and precise response. Again, this permits the patient to move in a safe and/or more natural manner.

Magnetorheologically Actuated Prosthetic Knee

Figure 4:
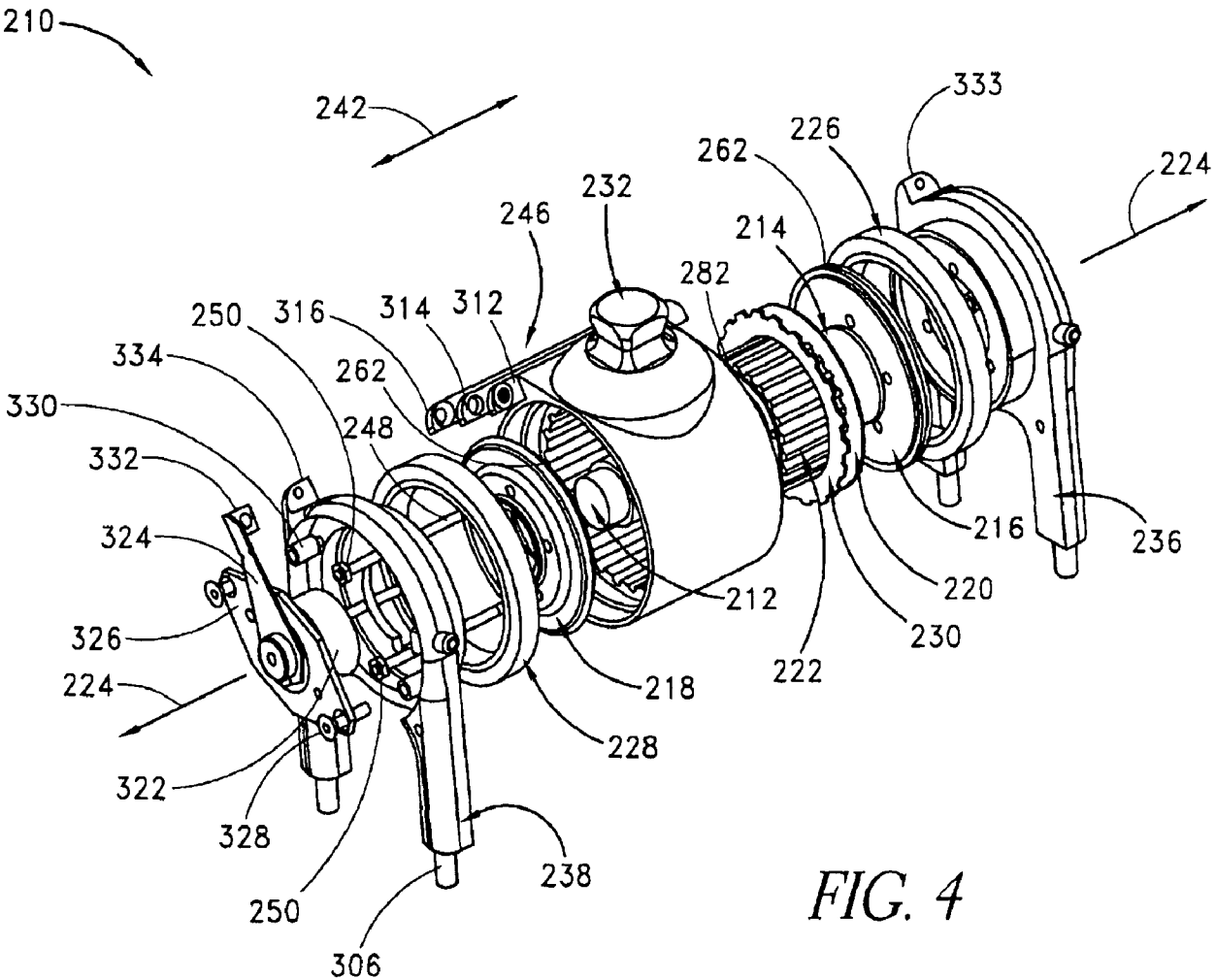
FIG. 4 is a detailed exploded perspective view of a magnetorheologically actuated prosthetic knee having features and advantages in accordance with one preferred embodiment of the present invention.
Figure 5:
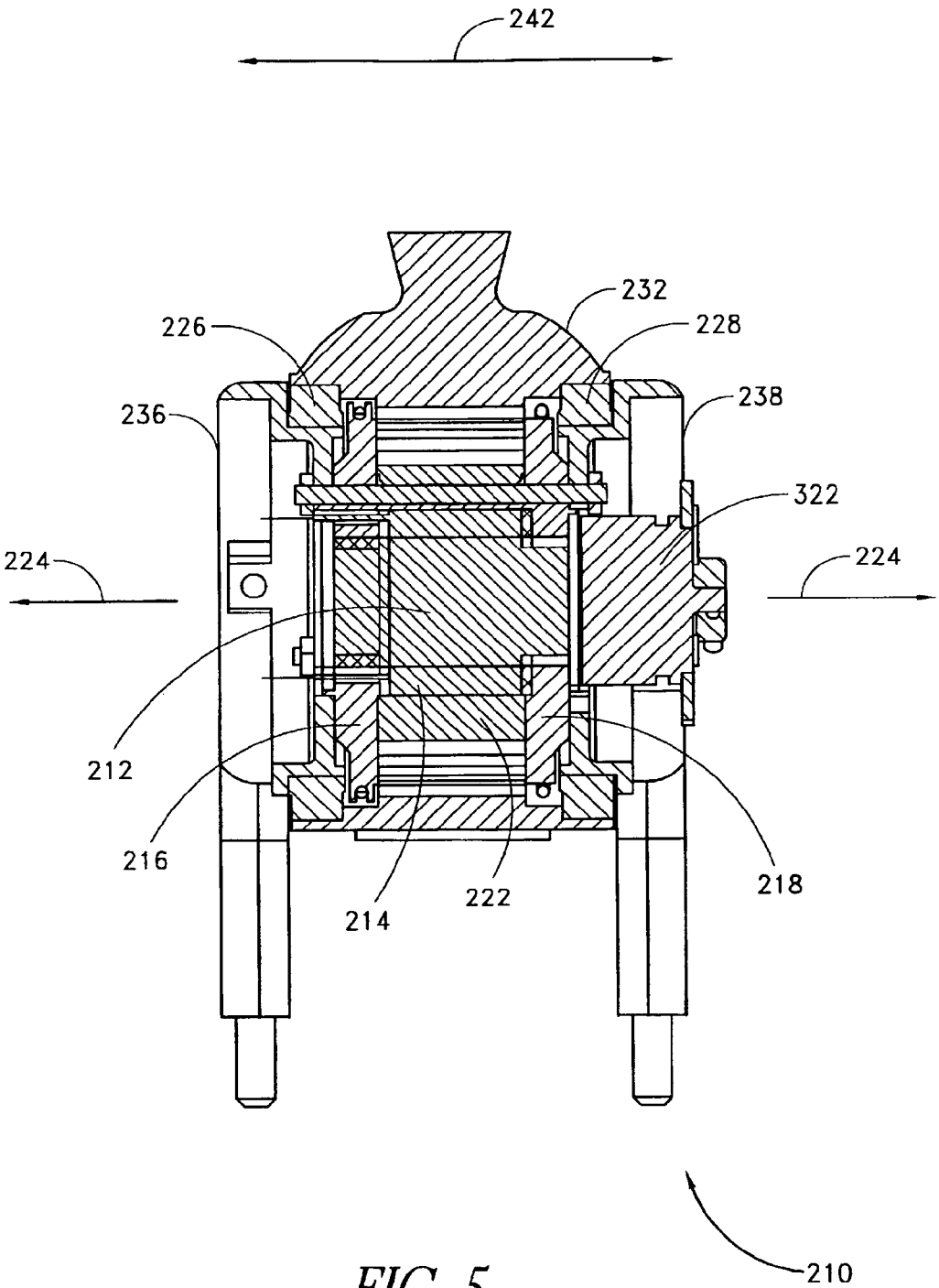
FIG. 5 is a cross section view of the prosthetic knee of FIG. 4.

FIGS. 4 and 5 show a controllable rotary prosthetic knee joint 210 having features and advantages in accordance with one preferred embodiment of the present invention. The prosthetic knee 210 generates controllable dissipative forces preferably substantially along or about the knee axis of rotation 224.

The electronically controlled knee 210 generally comprises a generally central core 212 in mechanical communication with a pair of rotatable side plates 216, 218, an electromagnet 214, a plurality of blades or rotors 220 in mechanical communication with a rotatable inner spline 222, a plurality of blades or stators 230 in mechanical communication with a rotatable outer spline 232, a pair of ball bearings 226, 228 for transferring rotary motion to a pair of outer side walls or forks 236, 238. The rotation is substantially about the knee axis of rotation 224.

The plurality of rotors 220 and stators 230 are preferably interspersed in an alternating fashion and the gaps or microgaps between adjacent blades 220 and 230 comprise thin lubricating films of a magnetorheological (MR) fluid, which thereby resides in the cavity or passage formed between the inner spline 222 and the outer spline 232. This preferred embodiment provides a controllable and reliable artificial knee joint, which advantageously has a wide dynamic torque range, by shearing the MR fluid in the multiple gaps or flux interfaces between adjacent rotors 220 and stators 230.

Preferably, end-threaded rods 248 and nuts 250 are used to secure selected components of the prosthetic knee 210, thereby allowing a straightforward assembly and disassembly procedure with a minimum of fasteners. Alternatively, or in addition, various other types of fasteners, for example, screws, pins, locks, clamps and the like, may be efficaciously utilized, as required or desired, giving due consideration to the goals of providing secure attachment, and/or of achieving one or more of the benefits and advantages as taught or suggested herein.

Core and Associated Side Plates (Magnetic Return Path)

Preferably, the core 212 and associated side plates 216, 218 are formed of a magnetically soft material of high flux saturation density and high magnetic permeability. Thus, when the electromagnet 214 is actuated a magnetic field, circuit or path is generated or created within the knee joint 210. In one preferred embodiment, the magnetic field passes longitudinally (parallel to the axis of rotation 224) through the central core 212, radially through the side plate 218, laterally (parallel to lateral direction 242) through the interspersed set of rotors 220 and stators 230 and the magnetorheological (MR) fluid, and radially through the side plate 216.

The orientation or positioning of the electromagnet 214 and the direction of current flow through it determines the polarity of the magnetic field, and thereby determines whether the magnetic field passes radially inwards or outwards through the side plate 218, and hence in the correspondingly opposite direction through the side plate 216. The portion of the magnetic field passing through the core 212 and side plates 216, 218 generally defines the magnetic return path while the active or functional magnetic field is generally defined by the magnetic path through the rotors 220, stators 230 and MR fluid residing therebetween.

Figure 8:
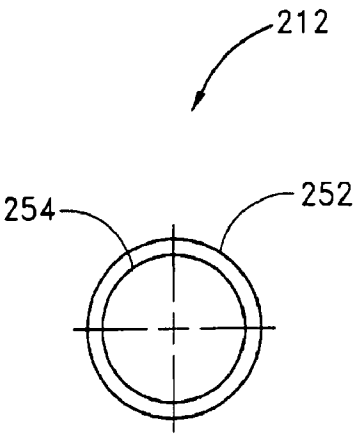
FIG. 8 is an end view of the core of FIG. 6.
Figure 7:
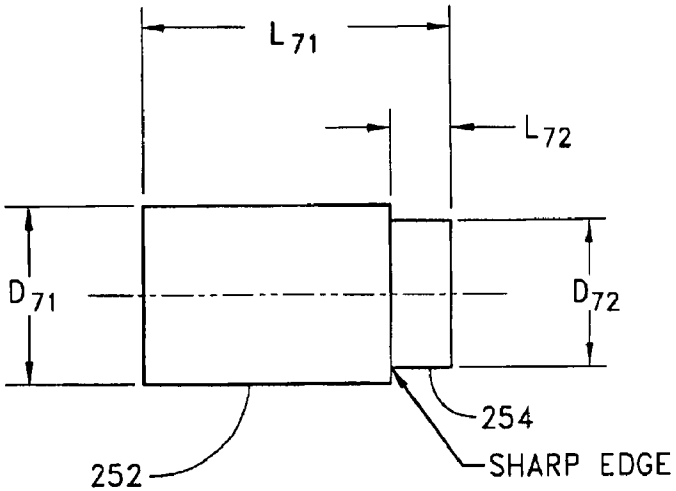
FIG. 7 is a side view of the core of FIG. 6.
Figure 6:
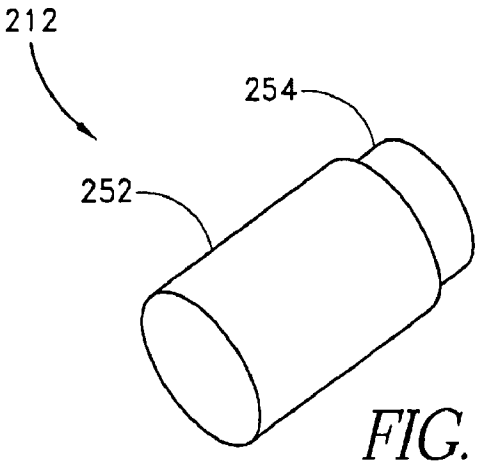
FIG. 6 is a perspective view of the core of FIG. 4 having features and advantages in accordance with one preferred embodiment of the present invention.

FIGS. 6-8 show one preferred embodiment of the core 212 of the knee joint 210. The core 212 is preferably generally cylindrical in shape and comprises a pair of cylindrical portions 252, 254 with the core portion 252 having a diameter larger than that of the core portion 254. The core portion 252 is sized and configured to matingly engage a corresponding cavity of the core side plate 216 while the core portion 254 is sized and configured to matingly engage a corresponding cavity of the core side plate 218. Thus, the core 212 rotates as the core side plates 216, 218 rotate. In other preferred embodiments, the core 212 may be sized, shaped and/or configured in alternate manners with efficacy, as required or desired, giving due consideration to the goals of providing a suitably compact, light weight and/or durable artificial knee, and/or of achieving one or more of the benefits and advantages as taught or suggested herein.

The core 212 is preferably fabricated form a material having a high saturation flux density, a high magnetic permeability and low coercivity. Advantageously, this facilitates in the construction of an artificial knee or brake that is compact and light weight, and also strong. In one preferred embodiment, the core 212 comprises an integral unit. In another preferred embodiment, the core 212 is formed of laminated sheets to advantageously reduce or minimize eddy current losses.

Preferably, the core 212 comprises an iron-cobalt (FeCo) high magnetic saturation alloy. In one preferred embodiment, the core 212 comprises the Iron-Cobalt High Magnetic Saturation Alloy, ASTM A-801, Type 1 Alloy, which specifies a composition with about 50% cobalt. For example, the core 212 may comprise Hiperco Alloy 50®, Permendur V™ or Vanadium [Pemendur] *Permendur*, as available from Principal Metals, or Vacoflux 50 as available from Vacuumschmelze of Hanau, Germany. In yet another preferred embodiment, the core 212 comprises a lower percentage of cobalt, for example, about 17%, available as Vacoflux 17 from Vacuumschmelze of Hanau, Germany. In other preferred embodiments, the core 212 can be efficaciously fabricated from alternate materials of high magnetic saturation, high magnetic permeability and low coercivity, as required or desired, giving due consideration to the goals of providing a suitably compact, light weight and/or durable prosthetic knee joint, and/or of achieving one or more of the benefits and advantages as taught or suggested herein.

In one preferred embodiment, the material comprising the core 212 has a saturation flux density of about 2.2 Tesla. Such a high saturation flux density is desirable because it allows a compact and light weight design. For example, if a material having a lower saturation flux density was utilized, the cross-sectional area of the return path through the core 212 in the direction of the applied magnetic field would have to be increased to achieve the same maximum torque and dynamic torque range. In other preferred embodiments, the core saturation flux density can be higher or lower, as needed or desired, giving due consideration to the goals of providing a suitably compact, light weight and/or durable prosthetic knee joint, and/or of achieving one or more of the benefits and advantages as taught or suggested herein.

Preferably, the core 212 is formed by machining followed by heat treatment in a hydrogen atmosphere to achieve optimal magnetic properties. In other preferred embodiments, the core 212 can be efficaciously fabricated from other techniques, for example, casting, forging, molding, laminating, among others, as required or desired, giving due consideration to the goals of providing desired magnetic properties and a suitably compact, light weight and/or durable artificial knee, and/or of achieving one or more of the benefits and advantages as taught or suggested herein.

In one preferred embodiment, and referring in particular to FIG. 7, the core 212 is dimensioned and configured such that the length $L_{71}$ is about 3.076 cm (1.211 inches), the length $L_{72}$ is about 0.61 cm (0.240 inches), the diameter $D_{71}$ is about 1.728 cm (0.6805 inches) and the diameter $D_{72}$ is about 1.424 cm (0.5605 inches). In another preferred embodiment, the diameter [$D_{71}$,] $D_{71}$ and/or diameter $D_{72}$ is about 1.91 cm (0.750 inches). In other preferred embodiments, the core 212 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

FIGS. 9-12 show one preferred embodiment of the core side plate or disk 216 of the prosthetic knee joint 210. The side plate 216 is preferably generally circular in shape and comprises a substantially central circular cavity or through hole 256 for matingly engaging the free end of the core portion 252. Preferably, this mating attachment is via an interference fit. Alternatively, other suitable shapes for the side plate 216 and cavity 256 may be efficaciously utilized, as needed or desired.

In one preferred embodiment, the other core side plate or disk 218 is sized, shaped and configured substantially the same as the side plate 216 of FIGS. 9-12, except that the substantially central circular cavity of the core side plate 218 is sized, shaped and configured to matingly engage the core portion 254, preferably via an interference fit. Thus, for purposes of clarity and brevity of disclosure it is to be understood that a detailed description of the core side plate 216 will suffice and embody most of the corresponding features of the core side plate 218.

Preferably, the side plate 216 comprises a plurality of approximately equally spaced through holes 258 arranged in a generally circular fashion to receive end-threaded rods or bolts and the like to secure the various components of the prosthetic knee 210. In one preferred embodiment, the side plate 216 comprises five holes 258. In another preferred embodiment, the side plate 216 comprises three holes 258. Alternatively, fewer or more holes 258 arranged in other fashions may be provided, as needed or desired.

The core side plate 216 preferably comprises a circular groove 260 to receive an O-ring 262 (FIG. 4), lip seal or gasket and the like. This provides a dynamic seal between the rotatable side plate 216 and the inner surface of the rotatable outer spline 232 and prevents leakage of MR fluid from the knee 210. The other side plate 218 is similarly configured to receive an O-ring 262 (FIG. 4) and provide a dynamic seal. In an alternative preferred embodiment, two grooves or flanges are provided on the inner surface of the outer spline 232 to receive O-rings or the like and provide a dynamic seal between the core side plates 216, 218 and the outer spline 232.

The O-rings 262 are fabricated from a suitable rubber material or the like such as Viton, Teflon and Neoprene among others. In one preferred embodiment, the O-rings 262 have an inner diameter of about 50 mm and a width of about 1.5 mm. In other preferred embodiments, the dynamic seals can be dimensioned and/or configured in alternate manners with efficacy, as required or desired, giving due consideration to the goals of providing reliable seals, and/or of achieving one or more of the benefits and advantages as taught or suggested herein.

The inner surface of the core side plate 216 preferably has a generally circular shoulder or step 264 for aligning or locating with the inner spline 222 (FIG. 4). The outer surface of the core plate 216 preferably has a generally ring-shaped shoulder or step 266 for aligning or locating with the outer fork 236 (FIG. 4). Optionally, the step 266 may include a cut 268 to allow clearance space for electrical wires or leads. Other holes around the central cavity 256 may be provided for passage of electrical wires or leads. Preferably, the outer surface of the core side plate 216 includes a tapered portion 270. This advantageously decreases weight, saves material and also provides clearance space to facilitate assembly.

The core side plate 216 is preferably fabricated form a material having a high saturation flux density, a high magnetic permeability and low coercivity. Advantageously, this facilitates in the construction of an artificial knee or brake that is compact and light weight, and also strong. In one preferred embodiment, the core plate 216 comprises an integral unit. In another preferred embodiment, the core plate 216 is formed of laminated sheets to advantageously reduce or minimize eddy losses.

Preferably, the core plate 216 comprises an iron-cobalt (FeCo) high magnetic saturation alloy. In one preferred embodiment, the core plate 216 comprises Iron-Cobalt High Saturation Alloy (ASTM A-801 Type 1 Alloy), which specifies a composition with about 50% cobalt. For example, the core [212] *plate 216* may comprise Hiperco Alloy 50®, Permendur V™ or Vanadium [Pemendur] *Permendur*, as available from Principal Metals, or Vacoflux 50 as available from Vacuumschmelze of Hanau, Germany. In yet another preferred embodiment, the core plate 216 comprises a lower percentage of cobalt, for example, about 17%, available as Vacoflux 17 from Vacuumschmelze of Hanau, Germany. In other preferred embodiments, the core plate 216 can be efficaciously fabricated from alternate soft magnetic materials or the like, as required or desired, giving due consideration to the goals of providing a suitably compact, light weight and/or durable prosthetic knee joint, and/or of achieving one or more of the benefits and advantages as taught or suggested herein.

In one preferred embodiment, the material comprising the core plate 216 has a saturation flux density of about 2.2 Tesla. Such a high saturation flux density is desirable because it allows a compact and light weight design. For example, if a material having a lower saturation flux density was utilized, the cross-sectional area of the return path through the core plate 216 in the direction of the applied magnetic field would have to be increased to achieve the same dynamic torque range. In other preferred embodiments, the core side plate saturation flux density can be higher or lower, as needed or desired, giving due consideration to the goals of providing a suitably compact, light weight and/or durable prosthetic knee joint, and/or of achieving one or more of the benefits and advantages as taught or suggested herein.

Preferably, the core side plate 216 is formed by machining followed by heat treatment in a hydrogen atmosphere to achieve optimal magnetic properties. In other preferred embodiments, the core side plate 216 can be efficaciously fabricated from other techniques, for example, casting, forging, molding, laminating, among others, as required or desired, giving due consideration to the goals of providing desired magnetic properties and a suitably compact, light weight and/or durable artificial knee, and/or of achieving one or more of the benefits and advantages as taught or suggested herein.

Figures 9, 10, 11, 12:
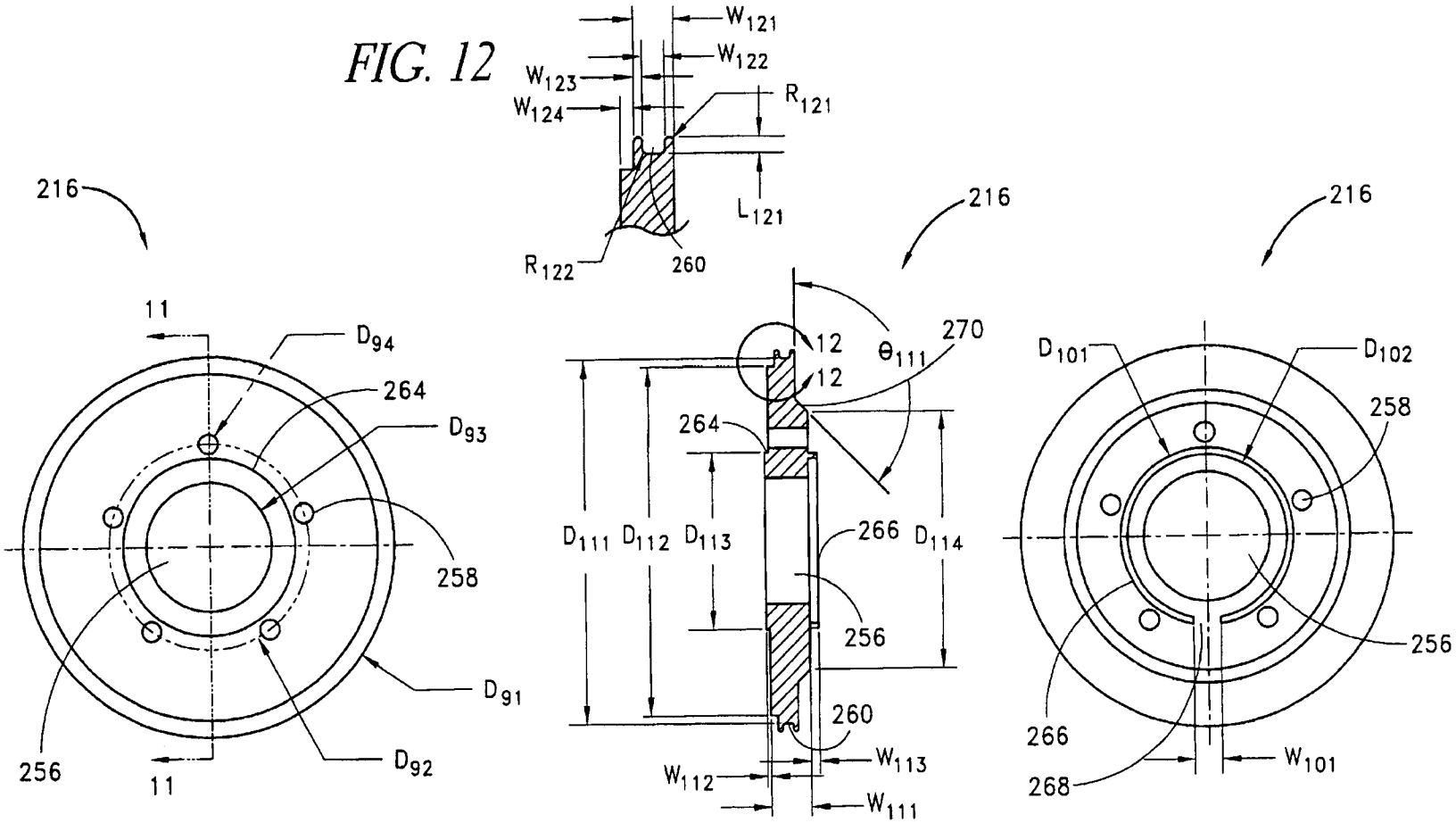
FIG. 9 is a front view of one of the core side plates of FIG. 4 having features and advantages in accordance with one preferred embodiment of the present invention.
FIG. 10 is a rear view of the core side plate of FIG. 9.
FIG. 11 is a cross section view along line 11-11 of FIG. 9.
FIG. 12 is an enlarged view of region 12-12 of FIG. 11.

In one preferred embodiment, and referring in particular to FIG. 9, the core side plate 216 is dimensioned and configured such that the major diameter $D_{91}$ is about 5.240 cm (2.063 inches), the blind-circle diameter $D_{92}$ is about 2.845 cm (1.120 inches), the diameter $D_{93}$ is about 1.727 cm (0.6800 inches) and the diameter $D_{94}$ is about 2.82 mm (0.111 inches). The diameter $D_{93}$ is preferably chosen to provide an interference fit between the central cavity 256 of the side plate 216 and the free end of the core portion 252. In another preferred embodiment, the diameter $D_{93}$ of the central cavity 256 is about 1.91 cm (0.750 inches). The corresponding central cavity of the other core side plate 218 has a diameter which is preferably chosen to provide an interference fit with the free end of the core portion 254. In other preferred embodiments, the core side plates 216, 218 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, and referring in particular to FIG. 10, the core side plate 216 is dimensioned and configured such that the diameter $D_{101}$ is about 2.43 cm (0.958 inches), the diameter $D_{102}$ is about 2.29 cm (0.900 inches) and the width $W_{101}$ is about 3.3 mm (0.13 inches). In other preferred embodiments, the core side plate 216 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, and referring in particular to FIG. 11, the core side plate 216 is dimensioned and configured such that the diameter $D_{111}$ is about 5.011 cm (1.973 inches), the diameter $D_{112}$ is about 4.801 cm (1.890 inches), the diameter $D_{113}$ is about 2.461 cm (0.969 inches), the diameter $D_{114}$ is about 3.56 cm (1.40 inches), the width $W_{111}$ is about 5.59 mm (0.220 inches), the width $W_{112}$ is about 0.508 mm (0.020 inches), the width $W_{113}$ is about 1.27 mm (0.050 inches) and the angle $\theta_{111}$ is about 135°. In other preferred embodiments, the core side plate 216 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, and referring in particular to FIG. 12, the core side plate 216 is dimensioned and configured such that the length $L_{121}$ is about 1.14 mm (0.045 inches), the width $W_{121}$ is about 2.79 mm (0.110 inches), the width $W_{122}$ is about 1.52 mm (0.060 inches), the width $W_{123}$ is about 0.64 mm (0.025 inches), the width $W_{124}$ is about 0.97 mm (0.038 inches), the radius of curvature $R_{121}$ is about 0.254 mm (0.010 inches) to about 0.127 mm (0.005 inches) and the radius of curvature $R_{122}$ is about 3.81 mm (0.15 inches). In other preferred embodiments, the core side plate 216 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

The core side plates 216, 218 are in mechanical communication with the pair of respective bearings 226, 228 (FIG. 4) for transferring rotary motion from the inner spline 222 (and hence rotors 220) to the pair of respective outer forks 236, 238 which in turn are mechanically connected to a pylon or prosthetic shin portion. Any one of a number of suitable bearings as known in the art may be used. In one preferred embodiment, the bearings 226, 228 comprise AST P/N B544DDXA ball bearings as available from The Torrington Company of Torrington, Conn.

The electromagnet or magnetic coil 214 (FIG. 4) generally circumscribes the core 212 and is preferably in mechanical communication with the core 212 and/or the core side plates 216, 218 so that the electromagnet 214 rotates along with the rotation of the core 212 and/or the core side plates 216, 218. The core 212 generally comprises a bobbin with winding or a coil. The number of turns or wraps of the winding is optimized. In one preferred embodiment, the winding comprises 340 turns or wraps. In other preferred embodiments fewer or more turns or wraps can be utilized with efficacy, as required or desired, giving due consideration to the goals of optimizing performance, and/or of achieving one or more of the benefits and advantages as taught or suggested herein.

The winding of the electromagnet 214 preferably comprises AWG 30 gauge copper magnet wire. In other preferred embodiments, the winding can comprise other types of materials with efficacy, as required or desired, giving due consideration to the goals of optimizing performance, and/or of achieving one or more of the benefits and advantages as taught or suggested herein.

Figure 14:
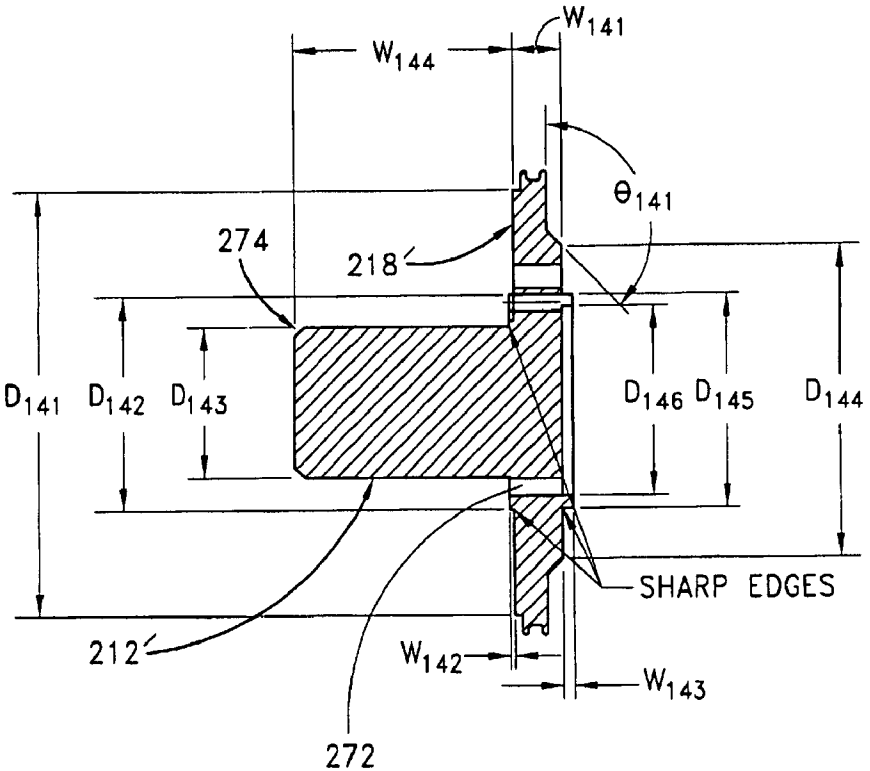
FIG. 14 is a cross section view along line 14-14 of FIG. 13.
Figure 13:
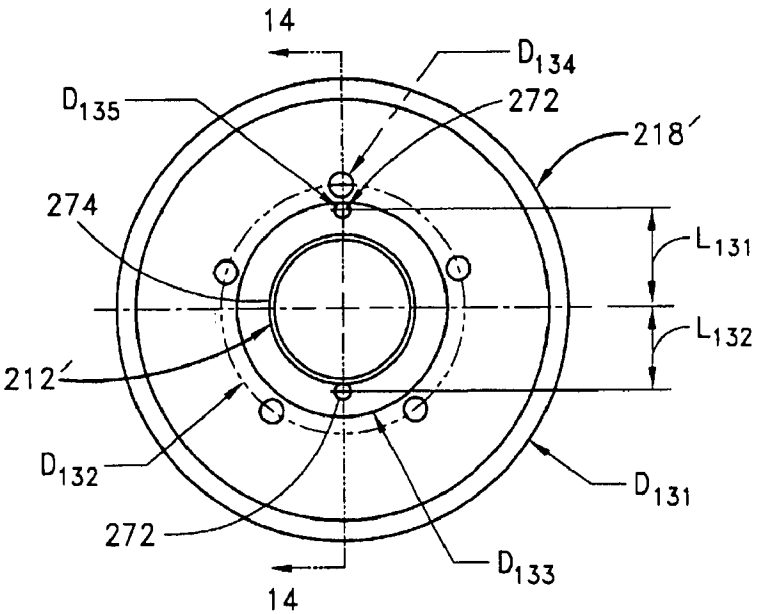
FIG. 13 is a front view of a combined core and associated side plate having features and advantages in accordance with one preferred embodiment of the present invention.

FIGS. 13 and 14 show one preferred embodiment of a core 212' having an integrally formed core side plate 218' for use in conjunction with the MR actuated knee joint of the present invention. If desired both core side plates may be integrally formed with the core 212'. The embodiment of FIGS. 13-14 has several features which have already been discussed above. Thus, for purposes of clarity and brevity of disclosure it is to be understood that a limited discussion of this embodiment as set forth below is sufficient.

The side plate 218' comprises a pair of holes 272 which permit passage of electrical wires or leads. The end of the core 218' has a tapered peripheral portion 274. This taper 274 facilitates in matingly engaging the other side plate 216 via an interference fit.

In one preferred embodiment, and referring in particular to FIG. 13, the core 212' and core side plate 218' are dimensioned and configured such that the major diameter $D_{131}$ is about 5.240 cm (2.063 inches), the blind-circle diameter $D_{132}$ is about 2.845 cm (1.120 inches), the diameter $D_{133}$ is about 2.46 cm (0.969 inches), the diameter $D_{134}$ is about 2.82 mm (0.111 inches), the diameter $D_{135}$ is about 1.78 mm (0.070 inches), the length $L_{131}$ is about 11.2 mm (0.440 inches) and the length $L_{132}$ is about 0.98 mm (0.385 inches). In other preferred embodiments, the core 212' and core side plate 218' may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, and referring in particular to FIG. 14, the core 212' and core side plate 218' are dimensioned and configured such that the diameter $D_{141}$ is about 4.801 cm (1.890 inches), the diameter $D_{142}$ is about 2.461 cm (0.969 inches), the diameter $D_{143}$ is about 1.728 cm (0.6805 inches), the diameter $D_{144}$ is about 3.56 cm (1.40 inches), the diameter $D_{145}$ is about 2.43 cm (0.958 inches), the diameter $D_{146}$ is about 2.16 cm (0.849 inches), the width $W_{141}$ is about 5.59 mm (0.220 inches), the width $W_{142}$ is about 0.508 mm (0.020 inches), the width $W_{143}$ is about 1.27 mm (0.050 inches), the width $W_{144}$ is about 2.52 cm (0.991 inches), the angle $\theta_{141}$ is about 135° and the tapered portion 274 has a length of about 0.508 mm (0.02 inches) at an angle of about 45°. In another preferred embodiment, the diameter $D_{143}$ is about 1.91 cm (0.750 inches). In other preferred embodiments, the core 212' and core side plate 218' may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

Inner Spline

Figure 16:
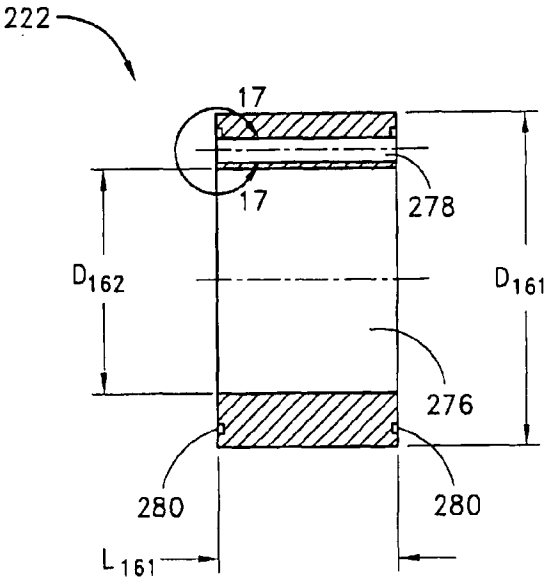
FIG. 16 is a cross section view along line 16-16 of FIG. 15.
Figure 17:
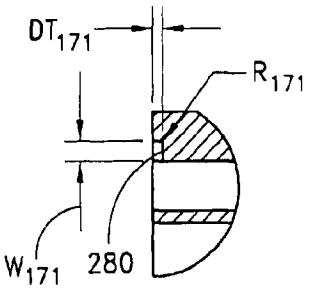
FIG. 17 is an enlarged view of region 17-17 of FIG. 16.
Figure 15:
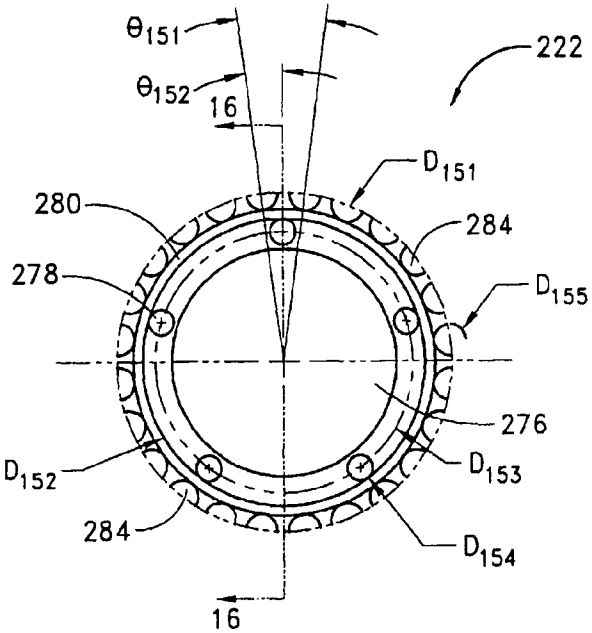
FIG. 15 is an end view of the inner spline of FIG. 4 having features and advantages in accordance with one preferred embodiment of the present invention.

FIGS. 15-17 show one preferred embodiment of the inner spline 222 of the prosthetic knee joint 210. The inner spline 222 is preferably generally cylindrical in shape and comprises a substantially central cylindrical cavity or through hole 276 for receiving the electromagnet or magnetic coil 214 (FIG. 4). Alternatively, other suitable shapes for the inner spline 222 and cavity 276 may be efficaciously utilized, as needed or desired.

Preferably, the inner spline 222 comprises a plurality of approximately equally spaced longitudinal through holes 278 arranged in a generally circular fashion to receive end-threaded rods or bolts and the like to secure selected components of the prosthetic knee 210, such as the core side plates 216, 218 and the inner spline 222. These holes 278 are generally aligned with corresponding holes 258 of the core side plates 216, 218. In one preferred embodiment, the inner spline 222 comprises five holes 278. In another preferred embodiment, the inner spline 222 comprises three holes 278. Alternatively, fewer or more holes 278 arranged in other fashions may be provided, as needed or desired.

The inner spline 222 preferably comprises a circular groove 260 at each end to receive respective O-rings 282 (FIG. 4) or gaskets and the like. This provides a static seal between the inner spline 222 and the side plates 216, 218, since these components rotate together during knee rotation, and prevents leakage of MR fluid from the knee 210. In an alternative preferred embodiment, a respective groove or flange is provided on the inner surfaces of either or both plates 216, 218 to receive O-rings or the like and provide a static seal.

The O-rings 282 are fabricated from a suitable rubber material or the like such as Viton, Teflon and Neoprene among others. In one preferred embodiment, the O-rings 282 have an inner diameter of about 30.5 mm (1.201 inches) and a width of about 0.76 mm (0.030 inches). In other preferred embodiments, the static seals can be dimensioned and/or configured in alternate manners with efficacy, as required or desired, giving due consideration to the goals of providing reliable seals, and/or of achieving one or more of the benefits and advantages as taught or suggested herein.

The outer surface of the inner spline 222 preferably has a plurality of approximately equally spaced longitudinal grooves 284 which are adapted to engage corresponding teeth of the rotors 220. In one preferred embodiment, the grooves 284 are generally semi-circular in shape. In another preferred embodiment, the grooves 284 are generally rectangular or square shaped with rounded corners. In other preferred embodiments, the grooves 284 can be efficaciously shaped and/or configured in alternate manners, as required or desired, giving due consideration to the goals of providing reliable load transmission from the rotors 220 to the inner spline 222, and/or of achieving one or more of the benefits and advantages as taught or suggested herein.

The inner spline 222 is preferably fabricated from titanium or a titanium alloy, and more preferably from [6A1-14V] *6A1-4V* titanium alloy. Advantageously, the use of titanium or titanium alloys provides a near zero magnetic permeability and a yet strong, hard surface with low weight to engage the rotors and transmit torque from them. An additional benefit is that the high resistivity of the material (titanium or titanium alloy) reduces energy losses due to induced eddy Currents. In other preferred embodiments, the inner spline 222 can be efficaciously fabricated from other metals, alloys, plastics, ceramics among others, as required or desired, giving due consideration to the goals of providing an inner spline 222 of near zero magnetic permeability, and a suitably compact, light weight and/or durable artificial knee, and/or of achieving one or more of the benefits and advantages as taught or suggested herein.

Preferably, the inner spline 222 is formed by machining. In other preferred embodiments, the inner spline 222 can be efficaciously fabricated from other techniques, for example, casting, forging, molding, among others, as required or desired, giving due consideration to the goals of providing a suitably compact, light weight and/or durable artificial knee, and/or of achieving one or more of the benefits and advantages as taught or suggested herein.

In one preferred embodiment, and referring in particular to FIG. 15, the inner spline 222 is dimensioned and configured such that the blind-circle major diameter $D_{151}$ is about 3.673 cm (1.446 inches), the diameter $D_{152}$ is about 3.119 cm (1.228 inches), the blind-circle diameter $D_{153}$ is about 2.845 cm (1.120 inches), the hole diameter $D_{114}$ is about 2.49 mm (0.098 inches), the groove curvature diameter $D_{155}$ is about 3.18 mm (0.125 inches), the angle $\theta_{151}$ is typically about 15° and the angle $\theta_{152}$ is typically about 7.5°. In other preferred embodiments, the inner spline 222 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, and referring in particular to FIGS. 16 and 17, the inner spline 222 is dimensioned and configured such that the major diameter $D_{161}$ is about 3.632 cm (1.430 inches), the diameter $D_{162}$ is about 2.464 cm (0.970 inches), the length $L_{163}$ is about 1.96 cm (0.771 inches), the depth $DT_{171}$ is about 0.51 mm (0.020 inches), the width $W_{171}$ is about 1.02 mm (0.040 inches) and the radius of curvature $R_{171}$ is between about 0.127 mm (0.005 inches) and 0.254 mm (0.010 inches). In other preferred embodiments, the inner spline 222 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

Rotors and Stators

Figure 18:
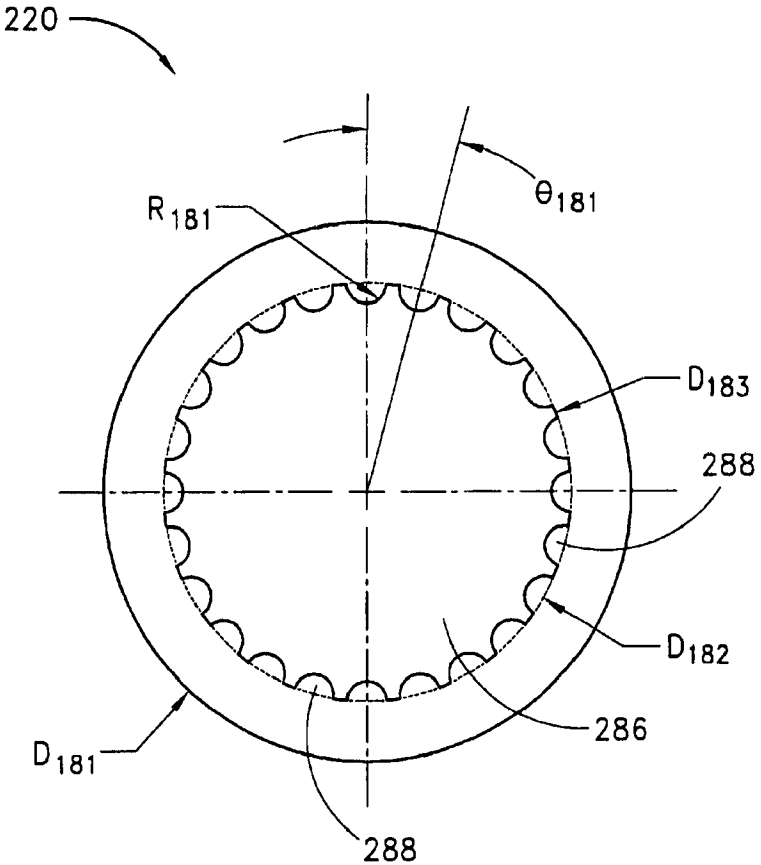
FIG. 18 is a front view of one of the rotors of FIG. 4 having features and advantages in accordance with one preferred embodiment of the present invention.
Figure 19:
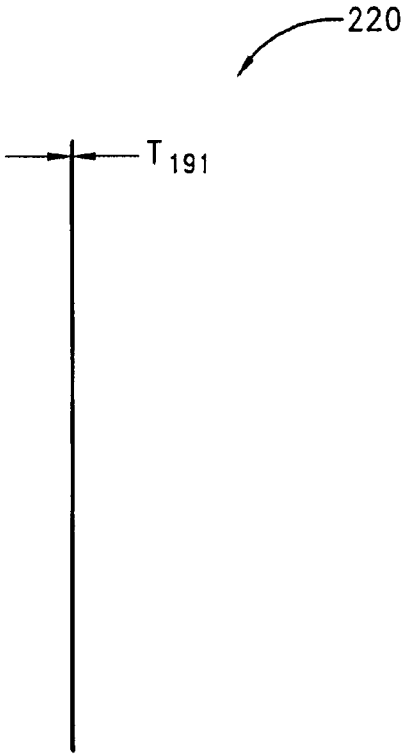
FIG. 19 is a side view of the rotor of FIG. 18.

FIGS. 18-19 show one preferred embodiment of one of the rotors or inner blades 220 of the prosthetic knee joint 210. The rotors 220 rotate with the rotation of the inner spline 222. The preferably annular or ring shaped thin rotor 220 is generally circular in shape and comprises a substantially central cavity or through hole 286 having a plurality of inwardly extending teeth 288 adapted to engage or mate with the inner spline grooves 284 (FIG. 15). Alternatively, the rotors 220 may be efficaciously shaped in other manners, as needed or desired.

In one preferred embodiment, the teeth 288 are generally semi-circular in shape. In another preferred embodiment, the teeth 288 are generally rectangular or square shaped with rounded corners. In other preferred embodiments, the teeth 288 can be efficaciously shaped and/or configured in alternate manners, as required or desired, giving due consideration to the goals of providing reliable load transmission from the rotors 220 to the inner spline 222, and/or of achieving one or more of the benefits and advantages as taught or suggested herein.

The rotors 220 are preferably fabricated from a magnetically soft material or the like which is mechanically hard to enhance durability and minimize wear. In one preferred embodiment, the rotors 220 are fabricated from blue temper steel. In another preferred embodiment, the rotors 220 are fabricated from non-grain oriented silicon steel (electric steel). In other preferred embodiments, the rotors 220 can be fabricated from alternate magnetically soft materials or the like with efficacy, as required or desired, giving due consideration to the goals of providing durable rotors 220, and/or of achieving one or more of the benefits and advantages as taught or suggested herein.

Preferably, the rotors 220 are fabricated from a material of moderate to high magnetic permeability, low or zero coercivity, and saturation flux density exceeding that of the magnetorheological fluid 134 (FIG. 3). Advantageously, this allows a compact, light weight design requiring less power dissipation in the electromagnet 214.

In one preferred embodiment, the rotors 220 are formed by wire electro-discharge machining (EDM). Advantageously, this permits a high degree of manufacturing precision and avoids or mitigates any backlash, jarring or play between the rotors 220 and inner spline 222 which may otherwise cause discomfort to the patient. In another preferred embodiment, the rotors 220 are formed by stamping techniques. In other preferred embodiments, the rotors 220 can be fabricated using alternate techniques with efficacy, as required or desired, giving due consideration to the goals of providing a natural and/or safe ambulation for the patient, and/or of achieving one or more of the benefits and advantages as taught or suggested herein.

In one preferred embodiment of the invention the rotors 220 are laterally fixed in position relative to the inner spline 222. That is, they are not displaceable in the direction 242 (FIG. 4) along the brake longitudinal axis 224 (FIG. 4). For this embodiment, the rotors 220 can be attached to the inner spline 222 by injecting resin, glue or the like along teeth engagements, laser welding the rotors 220 to the inner spline 222, shrink or thermal fitting the rotors 220 to the inner spline 222, bonding the rotors 220 to the inner spline 222, or clamping the rotors 220 to the inner spline 222 among other techniques. Advantageously, this also eliminates or mitigates backlash, jarring or play between the rotors 220 and inner spline 222 which may otherwise cause discomfort to the patient.

In one preferred embodiment, and referring in particular to FIGS. 18-19, the rotors 220 are dimensioned and configured such that the major diameter $D_{181}$ is about 4.80 cm (1.890 inches), the blind-circle diameter $D_{182}$ is about 3.678 cm (1.448 inches), the diameter $D_{183}$ is about 3.678 cm (1.448 inches), the tooth radius of curvature $R_{181}$ is typically about 1.57 mm (0.062 inches), the angle $\theta_{181}$ is typically about 15° and the rotor thickness $T_{191}$ is about 0.203 mm (0.008 inches). In other preferred embodiments, the rotors 220 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

Figure 20:
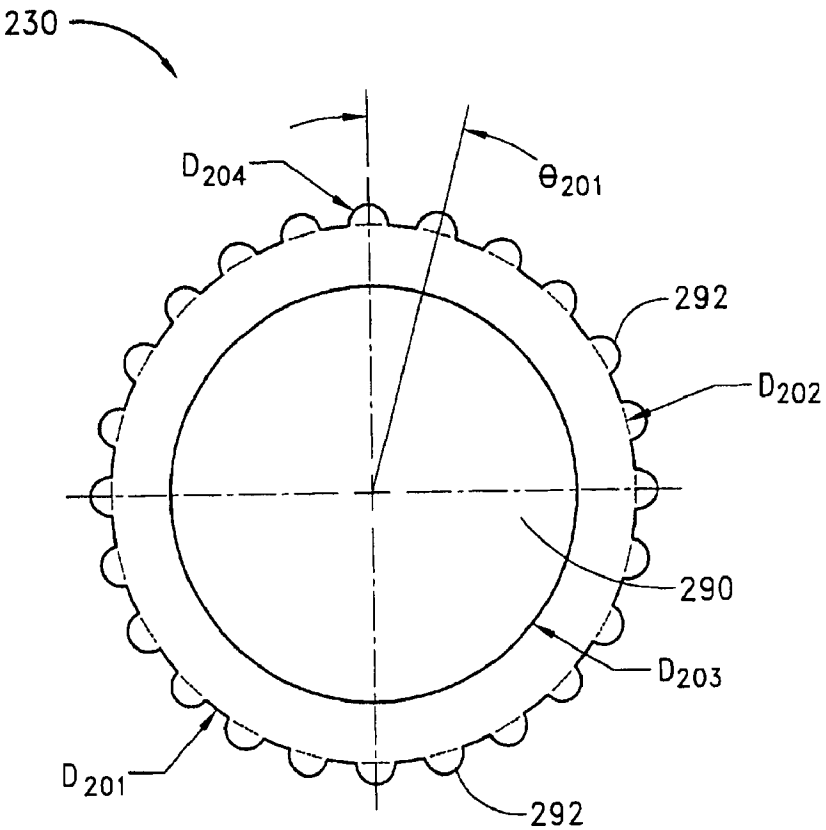
FIG. 20 is a front view of one of the stators of FIG. 4 having features and advantages in accordance with one preferred embodiment of the present invention.
Figure 21:
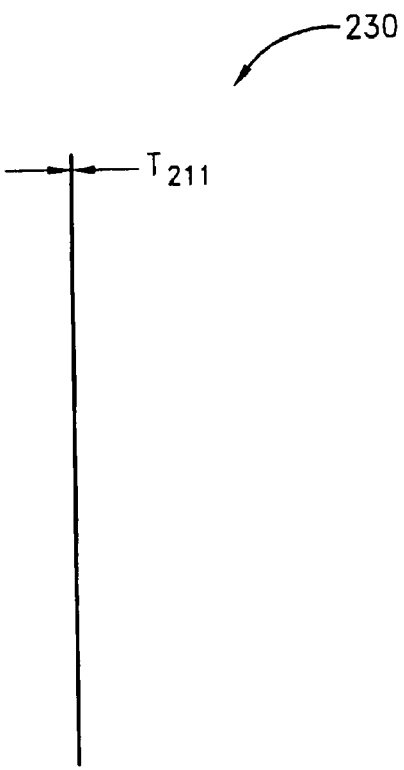
FIG. 21 is a side view of the stator of FIG. 20.

FIGS. 20-21 show one preferred embodiment of one of the stators or outer blades 230 of the prosthetic knee joint 210. The stators 230 rotate with the rotation of the outer spline 232. The preferably annular or ring shaped thin rotor 230 is generally circular in shape and comprises a substantially central cavity or through hole 290 adapted to non-contactingly receive the inner spline 222 and a plurality of outwardly extending teeth 292 on the stator outer periphery which are adapted to engage or mate with grooves on the interior of the outer spline 232. Alternatively, the stators 230 may be efficaciously shaped in other manners, as needed or desired.

In one preferred embodiment, the teeth 292 are generally semi-circular in shape. In another preferred embodiment, the teeth 292 are generally rectangular or square shaped with rounded corners. In other preferred embodiments, the teeth 292 can be efficaciously shaped and/or configured in alternate manners, as required or desired, giving due consideration to the goals of providing reliable engagement between the stators 230 to the outer spline 232, and/or of achieving one or more of the benefits and advantages as taught or suggested herein.

The stators 230 are preferably fabricated from a magnetically soft material or the like which is mechanically hard to enhance durability and minimize wear. In one preferred embodiment, the stators 230 are fabricated from blue temper steel. In another preferred embodiment, the stators 230 are fabricated from non-grain oriented silicon steel (electric steel). In other preferred embodiments, the stators 230 can be fabricated from alternate magnetically soft materials or the like with efficacy, as required or desired, giving due consideration to the goals of providing durable stators 230, and/or of achieving one or more of the benefits and advantages as taught or suggested herein.

Preferably, the stators 230 are fabricated from a material of moderate to high magnetic permeability, low or zero coercivity, and saturation flux density exceeding that of the magnetorheological fluid 134 (FIG. 3). Advantageously, this allows a compact, light weight design requiring less power dissipation in the electromagnet 214.

In one preferred embodiment, the stators 230 are formed by wire electro-discharge machining (EDM). Advantageously, this permits a high degree of manufacturing precision and avoids or mitigates any backlash, jarring or play between the stators 230 and outer spline 232 which may otherwise cause discomfort to the patient. In another preferred embodiment, the stators 230 are formed by stamping techniques. In other preferred embodiments, the stators 230 can be fabricated using alternate techniques with efficacy, as required or desired, giving due consideration to the goals of providing a natural and/or safe ambulation for the patient, and/or of achieving one or more of the benefits and advantages as taught or suggested herein.

In one preferred embodiment of the invention the stators 230 are laterally fixed in position relative to the outer spline 232. That is, they are not displaceable in the direction 242 (FIG. 4) along the brake longitudinal axis 224 (FIG. 4). For this embodiment, the stators 230 can be attached to the outer spline 232 by injecting resin, glue or the like along teeth engagements, laser welding the stators 230 to the outer spline 232, shrink or thermal fitting the stators 230 to the outer spline 232, bonding the stators 230 to the outer spline 232, or clamping the stators 230 to the outer spline 232 among other techniques. Advantageously, this also eliminates or mitigates backlash, jarring or play between the stators 230 and outer spline 232 which may otherwise cause discomfort to the patient.

In one preferred embodiment, and referring in particular to FIGS. 20-21, the stators 230 are dimensioned and configured such that the diameter $D_{201}$ is about 4.811 cm (1.894 inches), the blind-circle diameter $D_{202}$ is about 4.811 cm (1.894 inches), the diameter $D_{203}$ is about 3.683 cm (1.450 inches), the tooth curvature diameter $D_{204}$ is typically about 0.318 mm (0.125 inches), the angle $\theta_{201}$ is typically about 15° and the stator thickness $T_{211}$ is about 0.203 mm (0.008 inches). In other preferred embodiments, the stators 230 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, the rotors 220 and/or stators 230 can slide or are displaceable in the lateral direction 242 (FIG. 4) along the knee or brake longitudinal axis 224 (FIG. 4). Thus, when a magnetic field passes through the stack of rotors 220 and stators 230 in a direction substantially perpendicular to each rotor and stator surface both frictional damping and MR damping develop in response to the applied field. The frictional damping is the result of rotor surfaces rubbing against or mechanically contacting adjacent stator surfaces. Frictional damping increases with increasing field strength because the magnetized rotors 220 and stators 230 attract one another and increase the normal force (in the direction of the longitudinal axis 224) between adjacent rotors 220 and stators 230. This creates a "hybrid" magnetorheological (viscous) and frictional damping brake mechanism in which the prosthetic knee 210 of the present invention operates.

In one preferred embodiment, the rotor-stator friction component contributes about 10% or less to the total knee torque. In other preferred embodiments, the friction component can efficaciously contribute more or less to the total knee torque, as required or desired, giving due consideration to the goals of providing a wide dynamic torque range, and/or of achieving one or more of the benefits and advantages as taught or suggested herein.

In one preferred embodiment, the prosthetic knee brake of the present invention is configured so that the one or both of the core side plates 216 and 218 can slide or are displaceable in the lateral direction 242 along the knee or brake longitudinal axis 224, and hence can contribute to the frictional damping. Preferably, each core side plate 216 or 218 creates a friction component that contributes about 20% or less to the total knee torque. In other preferred embodiments, the friction component can efficaciously contribute more or less to the total knee torque, as required or desired, giving due consideration to the goals of providing a wide dynamic torque range, and/or of achieving one or more of the benefits and advantages as taught or suggested herein.

In one preferred embodiment, the rotors 220 and stators 230 are laterally (in the direction 242) rigidly fixed or attached in position relative to the splines 222 and 232, and hence the braking effect is substantially purely magnetorheological. Hence, as magnetic field strength increases, the normal force between adjacent rotor and stator surfaces remains zero or substantially zero, and frictional damping does not contribute to the total knee torque. Advantageously, this improves the brake fatigue life since possible wear through friction is eliminated or reduced.

Alternatively, some of the rotors 220 and/or stators 230 may be laterally fixed while others may be laterally displaceable, as required or desired, giving due consideration to the goals of providing a substantially natural feeling and/or safe prosthetic device, and/or of achieving one or more of the benefits and advantages as taught or suggested herein.

In one preferred embodiment, the prosthetic knee 210 of the present invention comprises forty rotors 220 and forty one stators 230 interspersed in an alternating fashion. This results in forty flux interfaces or fluid gaps in which the magnetorheological (MR) fluid resides. In another preferred embodiment, the number of rotors 220 is about ten to one hundred, the number of stators 230 is about eleven to one hundred one so that the number of MR fluid to rotor interfaces which produce braking in the presence of a magnetic field is twice the number of rotors. In yet another preferred embodiment, the number of rotors 220 is in the range of one to one hundred. In a further preferred embodiment, the number of stators 230 is in the range of one to one hundred. In other preferred embodiments, the number of rotors 220, stators 230 and/or flux interfaces may be alternately selected with efficacy, as needed or desired, giving due consideration to the goals of providing a wide dynamic torque range, and/or of achieving one or more of the benefits and advantages as taught or suggested herein.

Advantageously, the induced yield stress or viscous torque is proportional to the overlap area between a rotor-stator pair multiplied by twice the number of rotors (the number of MR fluid to rotor interfaces which produce braking torque in the presence of a magnetic field). This desirably allows the viscous torque or yield stress to be increased or decreased by selecting or predetermining the number of rotors 220 and/or stators 230 and/or the overlap or mating surface area between adjacent rotors 220 and/or stators 230. Another advantage is that this permits control over the overall size, that is radial size and lateral size, of the MR actuated prosthetic knee 210. For example, the overall knee configuration may be made radially larger and laterally slimmer while providing the same viscous torque range by appropriate selection of the number of flux interfaces and the overlap area of the shearing surfaces.

It is desirable to minimize the MR fluid gap between adjacent rotors 220 and stators 230 since the power needed to saturate the total MR fluid gap is a strong function of the gap size. Thus, advantageously, a smaller gap size renders the MR actuated brake 210 more efficient and reduces power consumption.

Preferably, the MR fluid gap size is also selected so that in the absence of an applied magnetic field only a viscous damping force or torque component is present from the shearing of MR fluid between adjacent rotor and stator surfaces. That is, there is no frictional torque component between the rotors 220 and stators 230 under zero-field conditions.

Accordingly, in one preferred embodiment, the power required to saturate the MR fluid is lowered and the dynamic range of the knee is enhanced by minimizing the MR fluid gap size. In this embodiment, the gap is not reduced so much that, under zero-field conditions, a normal force acts between adjacent rotor and stator surfaces, causing frictional rubbing. The absence of friction between rotors and stators enables the knee joint to swing freely, thereby providing a wider dynamic range. As a note, the viscous damping at zero-field does not increase dramatically with decreasing fluid gap because the MR fluid exhibits a property known as shear rate thinning in which fluid viscosity decreases with increasing shear rate.

In one preferred embodiment, the MR fluid gap size or width between adjacent rotors 220 and stators 230 is about 40 microns (μm) or less. In another preferred embodiment, the MR fluid gap size or width between adjacent rotors 220 and stators 230 is in the range from about 10 μm to about 100 μm. In other preferred embodiments, the MR fluid gap size can be alternately dimensioned and/or configured with efficacy, as required or desired, giving due consideration to the goals of providing an energy efficient prosthetic knee 210 having a wide dynamic torque range, and/or of achieving one or more of the benefits and advantages as taught or suggested herein.

In one preferred embodiment, the prosthetic knee of the invention comprises a single stator or blade 230 coupled to the outer spline 232 and no rotors or blades 220. Thus, two MR fluid gaps are created between the blade 230 and the core side plates 216, 218. Preferably, the size of the MR fluid gaps is minimized, as discussed above.

In accordance with another preferred embodiment of the present invention, the disk or blade shaped rotors and stators are replaced by tubular rotors and stators. The tubular rotors and stators preferably comprise a plurality of thin concentrically arranged, alternatingly rotating and fixed ferrous (or magnetically soft) generally cylindrical tubes. The gaps between the tubes comprises a magnetorheological fluid which is sheared during knee rotation. The magnetic flux activating the MR fluid travels radially outwards. The magnetic return path is closed through a tubular outer ferrous (or magnetically soft) housing and an axially located central core. The viscous torque developed by such a device is the sum of the viscous torques developed between each tubular rotor and stator pair. To minimize weight, volume and energy consumption, preferably, the tubular rotors and stators are made as thin as possible within the constraints primarily of the loading by the magnetic fluid shearing and manufacturing cost. Optionally, one or more of the tubular rotors and/or stators may be radially displaceable to provide a friction component to the total knee torque.

Magnetorheological Fluid

As indicated above, the magnetorheological fluid preferably comprises a plurality of iron, ferrous or magnetic particles suspended in fluid. These suspended particles form torque producing chains in response to an applied magnetic field. Thus, the magnetorheological (MR) fluid undergoes a rheology or viscosity change or variation which is dependent on the magnitude of the applied magnetic field. In turn, this variation in the bulk fluid viscosity determines the magnitude of the shearing force/stress or torque generated, and hence the level of damping or braking provided by the prosthetic knee 210. Typically, the bulk viscosity of the MR fluid increases with increasing strength of the applied field. By controlling the magnitude of this magnetic field, the rotary motion of the artificial limb is rapidly and precisely adjusted and/or controlled, for example, to control the flexion and extension during swing and stance phases to provide a more natural and safe ambulation for the amputee.

The magnetorheological fluid used in conjunction with the prosthetic knee of the preferred embodiments of the present invention can comprise any one of a number of commercially available or known MR fluids or magnetically controlled mediums. Preferably, the MR fluid possesses a high magnetic flux capacity and low magnetic reluctance and low viscosity while having a large magnetic field induced shearing stress so that, advantageously, the prosthetic knee of the invention provides a wide dynamic torque range.

The MR fluid between the rotor-stator surfaces preferably comprises a carrier fluid with polarizable ferrous or iron particles having a size on the order of a micron or few microns. Ideally the carrier fluid exhibits shear rate thinning behavior where carrier fluid viscosity decreases with increasing shear rate. This advantageously minimizes the viscous torque due to shearing of the MR fluid between each rotor-stator pair under zero-field conditions (that is, when the electromagnet is not energized), and hence allows for a larger operating torque range. Suitable candidates for carrier fluid include silicone oil, hydrocarbon oil, and water based fluids among others.

Outer Spline and Mounting Forks

FIGS. 22-25 show one preferred embodiment of the outer spline 232 of the prosthetic knee joint 210. The outer spline 232 is preferably generally cylindrical in shape and comprises a substantially central cylindrical cavity or through hole 284 for receiving the stators 230, the core side plates 216, 218 and the bearings 226, 228. Alternatively, other suitable shapes for the outer spline 232 and cavity 294 may be efficaciously utilized, as needed or desired.

The central surface of the cavity 294 preferably has a plurality of approximately equally spaced longitudinal grooves 296 which are adapted to engage corresponding teeth 292 of the stators 230. In one preferred embodiment, the grooves 296 are generally semi-circular in shape. In another preferred embodiment, the grooves 296 are generally rectangular or square shaped with rounded corners. In other preferred embodiments, the grooves 296 can be efficaciously shaped and/or configured in alternate manners, as required or desired, giving due consideration to the goals of providing engagement between the stators 230 to the outer spline 232, and/or of achieving one or more of the benefits and advantages as taught or suggested herein.

The outer spline cavity 294 preferably has a pair of generally circular shoulders or steps 298 with one on either side of the grooves 296 for aligning or locating with respective cores side plates 216, 218. In one preferred embodiment, two generally circular grooves or flanges are provided within the cavity 294 to receive O-rings or the like and provide a dynamic seal between the rotatable outer spline 232 and the rotatable core side plates 216, 218. The outer spline cavity 294 preferably further includes pair of generally circular shoulders or steps 300 with one on either side of respective shoulders 298 for aligning or locating with respective bearings 226, 228.

In one preferred embodiment, the outer spline 232 includes a pyramid stub or connector 302 at its top end 304 for facilitating connection of the prosthetic knee 210 to a stump socket or residual limb of the amputee. The pyramid connector 302 preferably provides a substantially nonrotatable coupling between the stump socket or residual limb and the outer spline 232, and hence the stators 230. Alternatively, other suitable connectors and fittings may be efficaciously used, as required or desired, giving due consideration to the goals of providing reliable attachment between the prosthetic knee 210 and the residual limb of the amputee, and/or of achieving one or more of the benefits and advantages as taught or suggested herein.

In one preferred embodiment, the pyramid stub 302 comprises titanium or a titanium alloy and the remainder of the outer spline 232 comprises anodized 7075-T6 aluminum alloy. Advantageously, the hard anodized aluminum alloy surface protects the surfaces of the outer spline grooves 296 against surface damage and hence eliminates or mitigates any backlash, jarring or play. In another preferred embodiment, the outer spline 232 is fabricated from titanium or a titanium alloy. In yet another preferred embodiment, the outer spline 232 is fabricated from anodized 7075-T6 aluminum alloy. In other preferred embodiments, the outer spline 232 can be efficaciously fabricated from other metals, alloys, plastics, ceramics among others, as required or desired, giving due consideration to the goals of providing a suitably strong, durable, light weight and/or substantially non-magnetic outer spline 232, and/or of achieving one or more of the benefits and advantages as taught or suggested herein.

Preferably, the outer spline 232 is formed by machining. In one preferred embodiment, a titanium or titanium block is threaded into a threaded cavity of the top end 304 of the outer spline 232, secured with Locktite and machined to form the pyramid stub 302, thereby allowing for proper juxtapositioning of the pyramid stub 302. In other preferred embodiments, the outer spline 232 can be efficaciously fabricated from other techniques, for example, casting, forging, molding, among others, as required or desired, giving due consideration to the goals of providing a suitably compact, light weight and/or durable artificial knee, and/or of achieving one or more of the benefits and advantages as taught or suggested herein.

Figure 23:
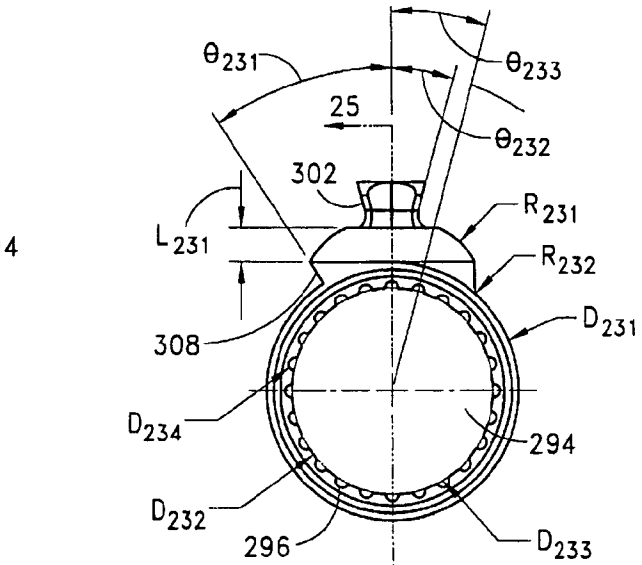
FIG. 23 is an end view of the outer spline of FIG. 22.
Figure 22:
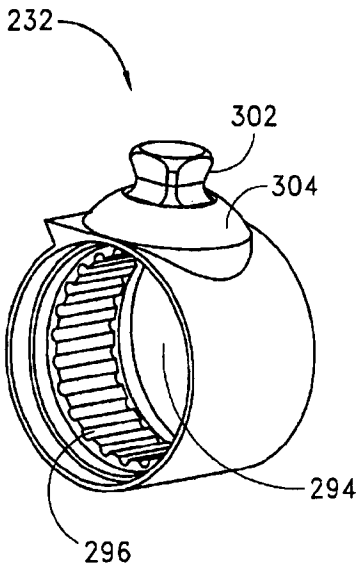
FIG. 22 is a perspective view of the outer spline of FIG. 4 having features and advantages in accordance with one preferred embodiment of the present invention.

In one preferred embodiment, and referring in particular to FIG. 23, the outer spline 232 is dimensioned and configured such that the major diameter $D_{231}$ is about 5.994 cm (2.360 inches), the diameter $D_{232}$ is about 4.813 cm (1.895 inches), the blind-circle diameter $D_{233}$ is about 4.811 cm (1.894 inches), the groove curvature diameter $D_{234}$ is about 3.20 mm (0.126 inches), the length $L_{231}$ is about 8.0 mm (0.315 inches), the angle $\theta_{231}$ is about 33.7°, the angle $\theta^{232}$ is about 15°, the angle $\theta_{233}$ is about 15°, the radius of curvature $R_{231}$ is about 2.40 cm (0.945 inches) and the radius of curvature $R_{232}$ is about 0.762 mm (0.030 inches). In other preferred embodiments, the outer spline 232 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

Figure 24:
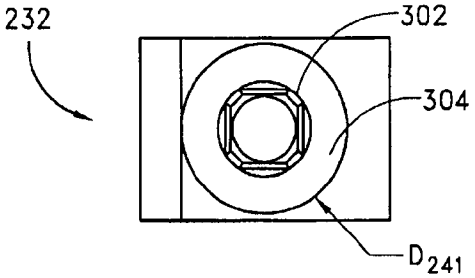
FIG. 24 is a top view of the outer spline of FIG. 22.
Figure 25:
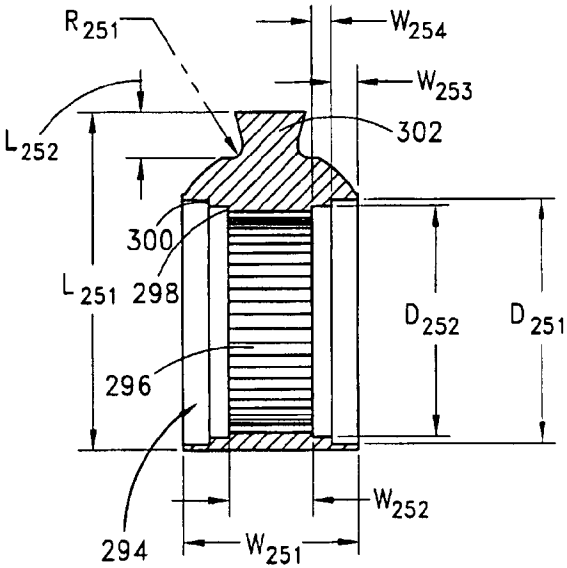
FIG. 25 is a cross section view along line 25-25 of FIG. 23.

In one preferred embodiment, and referring in particular to FIGS. 24-25, the outer spline 232 is dimensioned and configured such that the diameter $D_{241}$ is about 4.00 cm (1.575 inches), the diameter $D_{251}$ is about 5.715 cm (2.250 inches), the diameter $D_{252}$ is about 5.398 cm (2.125 inches), the length $L_{251}$ is about 7.861 cm (3.095 inches), the length $L_{252}$ is about 1.067 cm (0.420 inches), the width $W_{251}$ is about 4.171 cm (1.642 inches), the width $W_{252}$ is about 1.958 cm (0.771 inches), the width $W_{253}$ is about 6.35 mm (0.250 inches), the width $W_{254}$ is about 4.72 mm (0.186 inches) and the radius of curvature $R_{251}$ is about 3.05 mm (0.120 inches). In other preferred embodiments, the outer spline 232 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

The mounting forks 236, 238 (FIG. 4) of the magnetorheologically actuated prosthetic knee 210 are preferably in mechanical communication with the bearings 226, 228 respectively and transfer rotary motion to a pylon or artificial shin portion of the amputee. Threaded studs 306 or other suitable connectors or fasteners are used to facilitate connection of the mounting forks 236, 238 to a pylon or artificial shin portion of the amputee.

Preferably, the mounting forks 236, 238 are fabricated from anodized 7075-T6 aluminum alloy. In other preferred embodiments, the mounting forks 226, 238 can be efficaciously fabricated from other metals, alloys, plastics, ceramics among others, as required or desired, giving due consideration to the goals of providing suitably strong, durable, light weight and/or substantially non-magnetic mounting forks 226, 238, and/or of achieving one or more of the benefits and advantages as taught or suggested herein.

In one preferred embodiment, the mounting forks 236, 238 are formed by machining. In other preferred embodiments, the mounting forks 236, 238 can be efficaciously fabricated from other techniques, for example, casting, forging, molding, among others, as required or desired, giving due consideration to the goals of providing a suitably compact, light weight and/or durable artificial knee, and/or of achieving one or more of the benefits and advantages as taught or suggested herein.

In one preferred embodiment, and as shown in FIG. 4, the prosthetic knee 210 further comprises a flexion stop system or assembly comprising a cushioned stop or restraint assembly or system 246. The flexion stop system controls the maximum allowable flexion angle by physically limiting the rotation between the outer side forks 236, 238 and the outer spline 232, and hence the rotation of the knee joint.

The stop system 246 (FIG. 4) generally comprises a plurality of stops, bands or strips 312, 314 and 316. The bands 312 and 314 are attached to an angled outer surface 308 (see FIG. 23) of the outer spline 232 using screws or the like. The band 316 is attached to angled outer surfaces 333, 334 of the side forks 236, 238, respectively, using screws or the like.

The prosthetic knee 210 is preferably configured so that at a predetermined maximum flexion angle the band 316 contacts or stops against the band 314 and prevents or restricts further knee rotation. Preferably, the band 314 comprises a resilient material to provide a shock absorbing, cushioning and/or dissipating effect. Similarly, the prosthetic knee of the preferred embodiments can comprise a shock absorbing extension stop, as needed or desired.

In one preferred embodiment, the flexion stop system of the present invention is configured to allow a maximum flexion angle of about 140°. In another preferred embodiment, the flexion stop system of the present invention is configured to allow a maximum flexion angle in the range from about 125° to about 150°. In other preferred embodiments, the maximum flexion angle can be efficaciously varied, as needed or desired, depending on the ambient conditions, activity and activity level, among other factors.

In one preferred embodiment, the stop 314 is fabricated from rubber and the stops 312, 316 are fabricated from titanium or a titanium alloy. In other preferred embodiments, the stops 312, 314, 316 can be efficaciously fabricated from other materials as required or desired, giving due consideration to the goals of providing a suitably strong, durable, light weight and/or cushioned flexion stop, and/or of achieving one or more of the benefits and advantages as taught or suggested herein.

In one preferred embodiment, the stops 312, 314, 316 have a major length of about 6.00 cm (2.363 inches) and a major width of about 5.99 mm (0.236 inches). In other preferred embodiments, the stops 312, 314, 316 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, the prosthetic knee 210 comprises an angle sensing potentiometer 322 (FIG. 4). The potentiometer 322 is connected to an arm 324 and a mounting plate 326. The mounting plate 326 is connected to the fork 238 utilizing screws 328 or the like and spacers 330. An end 332 of the arm 324 is mechanically connected to the angled outer surface 334 of the fork 238 utilizing suitable screws or the like.

In one preferred embodiment of the present invention, the prosthetic knee 210 further comprises an extension assist to help straighten the leg by urging or biasing the leg to extension by applying a controlled torque or force. Any one of a number of devices, such as a spring-loaded extension assist, as known in the art may be used in conjunction with the present invention.

Preferably, a feedback control system is provided to control and monitor the actuations of the magnetorheologically actuated prosthetic knee of the preferred embodiments of the present invention. The control system generally comprises a central controller or microprocessor and memory, one or more force, torque and angle sensors, a power source (such as a battery or the like) and other associated hardware and software. An outer housing or casing is preferably provided to house and/or protect the various components of the prosthetic knee of the preferred embodiments and the control system. A suitable cosmetic covering is also preferably provided over the outer housing.

Certain Operational Features and Advantages

The electronically controlled magnetorheologically actuated prosthetic knee of the preferred embodiments provides high-speed instantly responsive control of knee movement, yet is robust and affordable for the amputee. The preferred embodiments advantageously provide improved stability, gait balance and energy efficiency for amputees and simulates and/or closely recreates the dynamics of a natural knee joint.

During operation, the electromagnet or magnetic coil 214 is actuated, as needed, by a selected or predetermined electrical signal, voltage or current to generate an active variable magnetic field passing substantially perpendicularly to the plurality of rotor and stator surfaces and through the MR fluid or film between adjacent rotors 220 and stators 230 to generate a variable damping torque (or rotary resistive force) which precisely and accurately controls the rotary motion of the prosthetic knee 210. As discussed above, in accordance with one preferred embodiment, the torque comprises a frictional damping component.

Desirably, the MR actuated prosthetic knee 210 of the preferred embodiments provides a rapid and precise response. The materials in MR particles respond to the applied magnetic field within milliseconds, thereby allowing for real-time control of the fluid rheology and the knee motion. This facilitates in permitting the patient to move in a safe and/or more natural manner.

Advantageously, the viscous damping torque is generated by shearing of the MR fluid. Hence, there is no or negligible pressure build-up or change within the MR actuated prosthetic knee 210 of the present invention. This substantially eliminates or reduces the chances of fluid leakage and failure of the knee, and hence desirably adds to the safety. Moreover, costly and/or relatively complex components such as pressure bearings and the like need not be utilized to provide a reliable seal.

Another advantage is that the plurality of shearing surfaces or flux interfaces between adjacent rotors 220 and stators 230 behave like a torque multiplier and allow the viscous torque level (and/or frictional torque) to be stepped up to a desired maximum value without the use of an additional transmission or other auxiliary component. Moreover, the flexibility in selecting the overlap surface area between adjacent rotors 220 and stators 230 can also increase or decrease the maximum attainable viscous torque (and/or frictional torque). Thus, desirably a wide dynamic torque or torsional resistance range can be provided, as needed or desired, which adds to the versatility of the invention without adding substantially to system size, weight and complexity.

In one preferred embodiment, the prosthetic knee of the present invention provides a maximum dynamic torque of about 40 Newton-meters (N-m). In another preferred embodiment, the prosthetic knee of the present invention provides a dynamic torque in the range from about 0.5 N-m to about 40 N-m. In yet another preferred embodiment, the prosthetic knee of the present invention provides a dynamic torque in the range from about 1 N-m to about 50 N-m. In other preferred embodiments, the prosthetic knee of the present invention can provide other dynamic torque ranges with efficacy, as needed or desired, giving due consideration to the goals of achieving one or more of the benefits and advantages as taught or suggested herein.

In one preferred embodiment, the prosthetic knee of the present invention precisely controls the knee rotation, during extension and flexion phases, between full extension and a flexion angle of about 140°. In another preferred embodiment, the prosthetic knee of the present invention precisely controls the knee rotation, during extension and flexion phases, between full extension and a flexion angle in the range from about 125° to about 150°. In other preferred embodiments, the prosthetic knee of the present invention can provide other knee rotation ranges with efficacy, as needed or desired, giving due consideration to the goals of achieving one or more of the benefits and advantages as taught or suggested herein.

Also advantageously, the optimized thinness of the MR fluid gap between adjacent rotors 220 and stators 230 provides a higher maximum torque, a wider dynamic torque range and requires less energy consumption, preferably about 10 Watts or less. This adds to the efficiency and practicality of the MR actuated prosthetic knee 210 of the present invention and also saves on cost since a lower wattage and/or less complex power source can be used.

Other Preferred Embodiments

FIGS. 26 to 51 show several preferred embodiments having features and advantages in accordance with the present invention. For purposes of clarity and brevity of disclosure only certain features of these embodiments are discussed below and it is to be understood that other features are obvious from the drawings and/or are embodied in the description of the preferred embodiments as set forth above.

Figure 26:
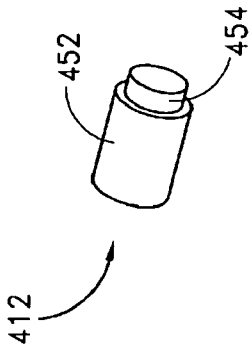
FIG. 26 is a perspective view of a core having features and advantages in accordance with one preferred embodiment of the present invention.
Figure 28:
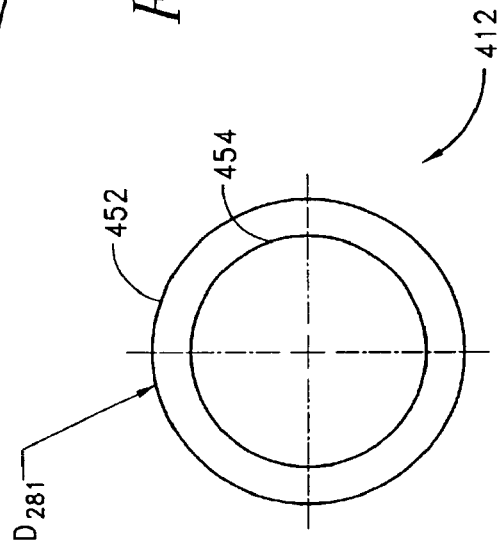
FIG. 28 is an end view of the core of FIG. 26.
Figure 27:
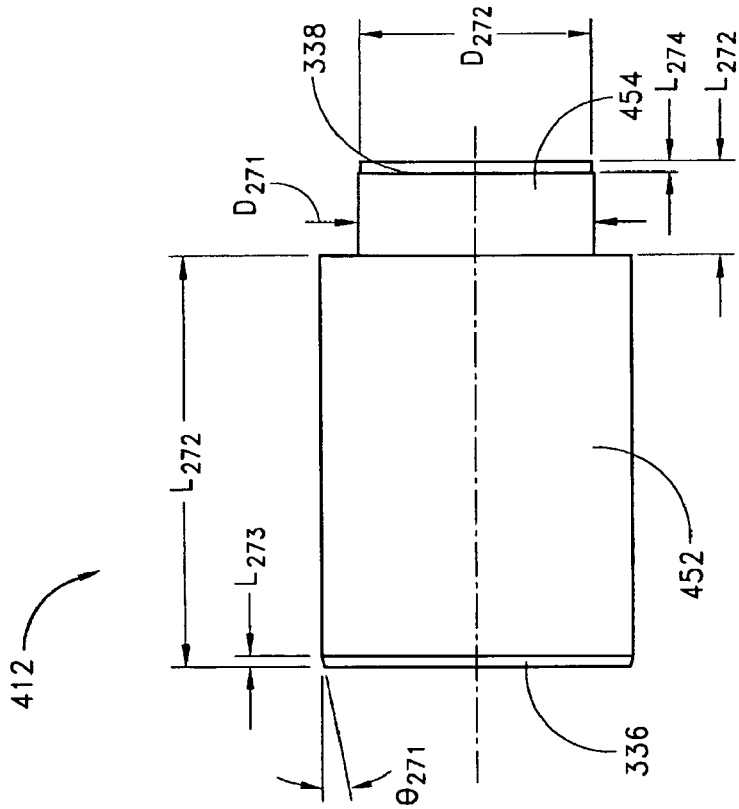
FIG. 27 is a side view of the core of FIG. 26.
Figure 29:
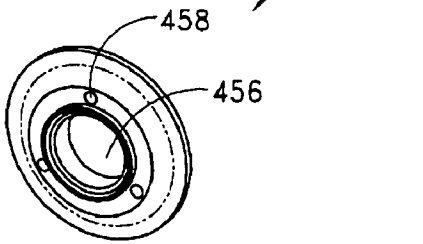
FIG. 29 is a perspective view of a first core side plate having features and advantages in accordance with one preferred embodiment of the present invention.
Figure 32:
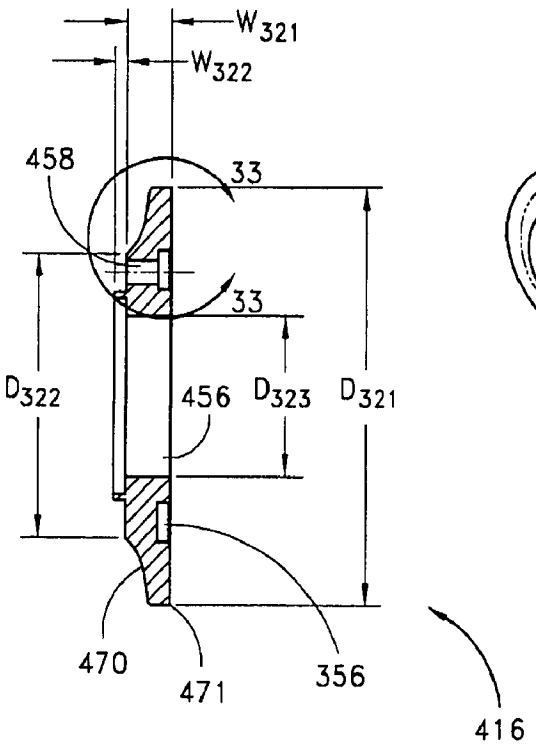
FIG. 32 is a cross section view along line 32-32 of FIG. 31.

FIGS. 26-28 show one preferred embodiment of a substantially central core 412 of a magnetorheologically actuated prosthetic knee of the present invention. The core 412 preferably comprises a beveled or tapered surface 336 and a shoulder or step 338 at respective ends of respective core portions 452, 454 to facilitate mating engagement or mechanical connection with associated core side plates 416, 418 (shown in FIGS. 29-36). Thus, the core 412 rotates as the side plates 416, 418 rotate.

Preferably, the core 412 comprises an iron-cobalt (FeCo) high magnetic saturation alloy. In one preferred embodiment, the core 412 comprises Iron-Cobalt High Saturation Alloy (ASTM A-801 Type 1 Alloy), which specifies a composition with about 50% cobalt. For example, the core [212] *412* may comprise Hiperco Alloy 50®, Permendur V™ or Vanadium [Pemendur] *Permendur*, as available from Principal Metals, Vacoflux 50 as available from Vacuumschmelze of Hanau, Germany.

The core 412 is preferably formed by machining followed by heat treatment in a dry hydrogen atmosphere to achieve optimal magnetic properties. The core 412 is annealed in a dry hydrogen atmosphere preferably for about five hours at a temperature of about 820° Celsius. The core 412 is then cooled in a dry hydrogen atmosphere at about 150° Celsius/hour until a temperature of about 200° Celsius is reached. Care is taken to avoid contamination during heat treatment and any grease, oil, fingerprints and the like are removed using acetone or other suitable cleaning solvents. During heat treatment, the core 412 is preferably separated from the core side plates 416 and 418 to avoid any possible welding between the components.

In one preferred embodiment, and referring in particular to FIGS. 27 and 28, the core 412 is dimensioned and configured such that the length $L_{271}$ is about 2.517 cm (0.991 inches), the length $L_{272}$ is about 5.56 mm (0.220 inches), the length $L_{273}$ is about 0.51 mm (0.020 inches), the length $L_{274}$ is about 0.51 mm (0.020 inches), the diameter $D_{271}$ is about 1.424 cm (0.5605 inches), the diameter $D_{272}$ is about 1.415 cm (0.557 inches), the angle $\theta_{271}$ is about 10° and the diameter $D_{281}$ is about 1.88 cm (0.740 inches). In other preferred embodiments, the core 412 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

Figure 37:
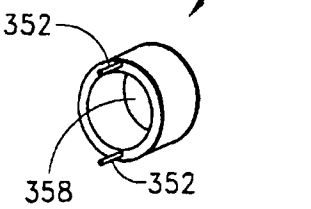
FIG. 37 is a perspective view of a magnetic coil having features and advantages in accordance with one preferred embodiment of the present invention.
Figure 39:
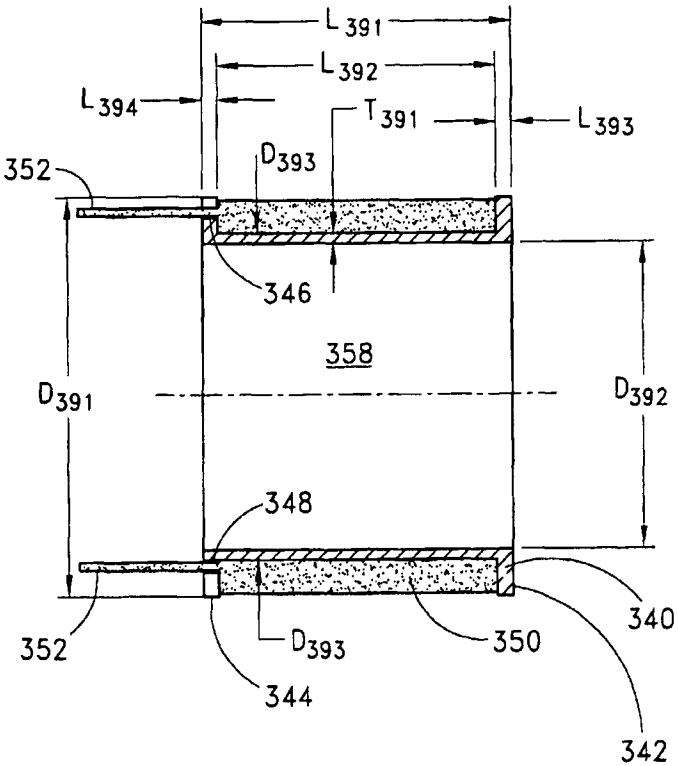
FIG. 39 is a cross section view along line 39-39 of FIG. 38.
Figure 38:
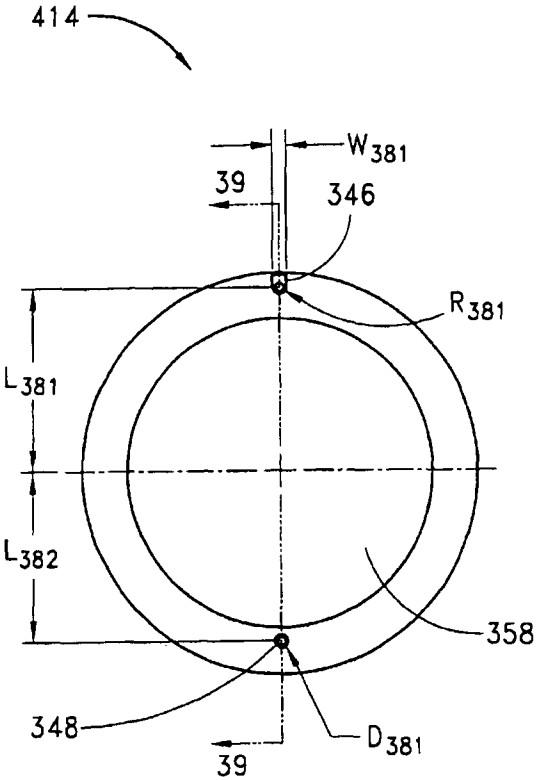
FIG. 38 is an end view of the magnetic coil of FIG. 34.
Figure 40:
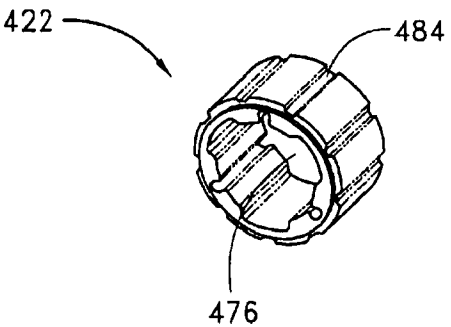
FIG. 40 is a perspective view of an inner spline having features and advantages in accordance with one preferred embodiment of the present invention.
Figure 42:
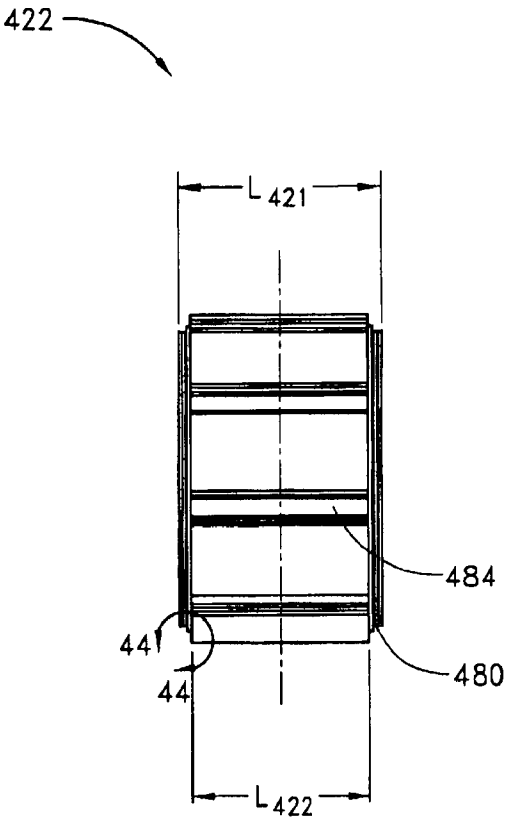
FIG. 42 is a side view of the inner spline of FIG. 40.

FIGS. 29-33 show one preferred embodiment of a core side plate 416 of a magnetorheologically actuated prosthetic knee of the present invention. The core side plate 416 preferably comprises a substantially central cavity or through hole 456 adapted to matingly form an interference fit with the end of the core portion 452 (FIGS. 26-28) and three approximately equally spaced through holes 458 arranged in a generally circular fashion to receive bolts or the like to fasten the various components of the prosthetic knee. The core side plate 416 further comprises a generally circular groove or recess 356 adapted to engage or mechanically connect with a flange of the electromagnet 414 (FIGS. 37-39). Thus, the electromagnet or magnetic coil 414 rotates as the core side plate 416 rotates.

Preferably, tapers or tapered surfaces or portions 470, 471 are provided on respective outer and inner surfaces of the core side plate 416. This advantageously decreases weight, saves material and also provides clearance space to facilitate assembly. The rotatable core side plate 416 forms a dynamic seal with a rotatable outer spline utilizing an O-ring or the like provided within a groove or flange of the outer spline.

Preferably, the core side plate 416 comprises an iron-cobalt (FeCo) high magnetic saturation alloy. In one preferred embodiment, the core side plate 416 comprises Iron-Cobalt High Saturation Alloy (ASTM A-801 Type 1 Alloy), which specifies a composition with about 50% cobalt. For example, the core [212] *side plate 416* may comprise Hiperco Alloy 50®, Permendur V™ or Vanadium [Pemendur] *Permendur*, as available from Principal Metals, Vacoflux 50 as available from Vacuumschmelze of Hanau, Germany.

The core side plate 416 is preferably formed by machining followed by heat treatment in a dry hydrogen atmosphere to achieve optimal magnetic properties. The core side plate 416 is annealed in a dry hydrogen atmosphere preferably for about five hours at a temperature of about 820° Celsius. The core side plate 416 is then cooled in a dry hydrogen atmosphere at about 150° Celsius/hour until a temperature of about 200° Celsius is reached. Care is taken to avoid contamination during heat treatment and any grease, oil, fingerprints and the like are removed using acetone or other suitable cleaning solvents. During heat treatment, the core side plate 416 is preferably separated from the core 412 to avoid any possible welding between the components.

In one preferred embodiment, and referring in particular to FIGS. 30-33, the core side plate 416 is dimensioned and configured such that the diameter $D_{301}$ is about 3.353 cm (1.320 inches), the diameter $D_{302}$ is about 2.461 cm (0.969 inches), the blind-circle diameter $D_{311}$ is about 2.845 cm (1.120 inches), the diameter $D_{312}$ is about 2.43 cm (0.958 inches), the diameter $D_{313}$ is about 2.29 cm (0.900 inches), the hole diameter $D_{314}$ is about 2.95 mm (0.116 inches), the angle $\theta_{311}$ is typically 120°, the diameter $D_{321}$ is about 4.80 cm (1.890 inches), the diameter $D_{322}$ is about 3.30 cm (1.300 inches), the diameter $D_{323}$ is about 1.88 cm (0.740 inches), the width $W_{321}$ is about 5.59 mm (0.220 inches), the width $W_{322}$ is about 1.27 mm (0.050 inches), the width $W_{331}$ is about 2.54 mm (0.100 inches), the width $W_{332}$ is about 0.508 mm (0.020 inches), the width $W_{333}$ is about 1.52 mm (0.060 inches), the radius of curvature $R_{331}$ is about 6.35 mm (0.250 inches), the radius of curvature $R_{332}$ is about 0.254 mm (0.010 inches), the angle $\theta_{331}$ is about 30° and the angle $\theta_{332}$ is about 10°. In other preferred embodiments, the core side plate 416 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

Figure 34:
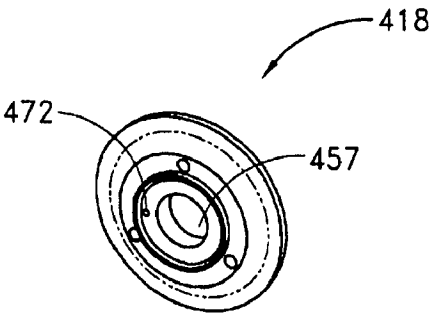
FIG. 34 is a perspective view of a second core side plate having features and advantages in accordance with one preferred embodiment of the present invention.
Figure 36:
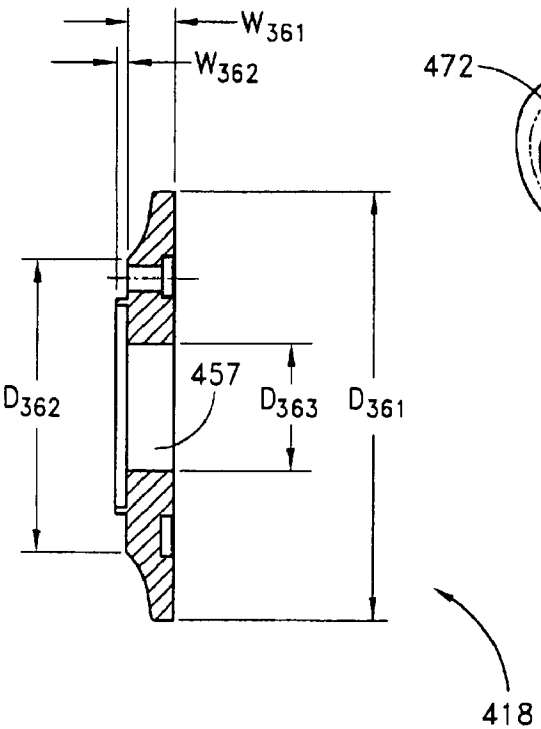
FIG. 36 is a cross section view along line 36-36 of FIG. 35.
Figure 35:
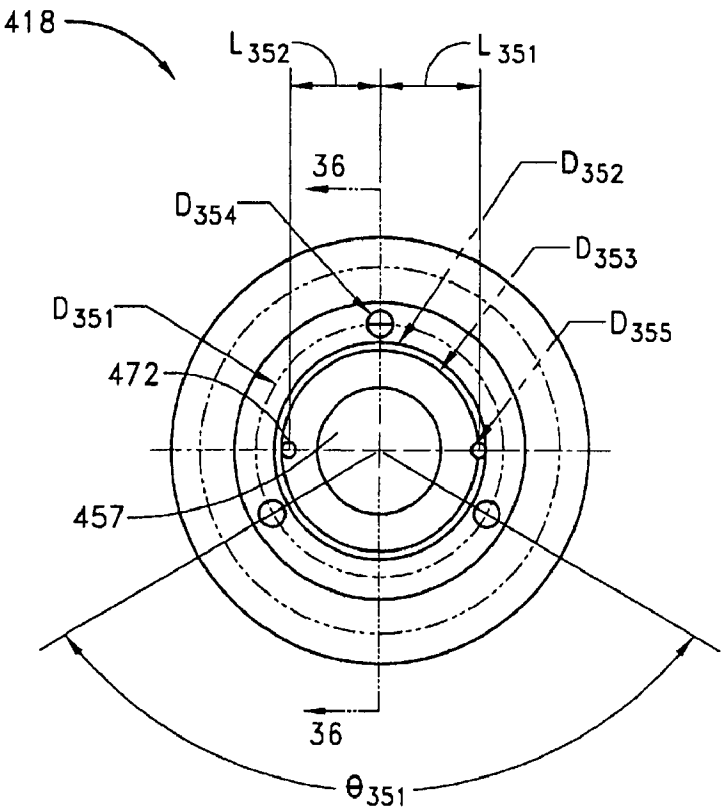
FIG. 35 is a rear view of the core side plate of FIG. 34.

FIGS. 34-36 show one preferred embodiment of a second core side plate 418 of a magnetorheologically actuated prosthetic knee of the present invention. The core side plate 418 is substantially the same as the first core side plate 416 except that it comprises a substantially central cavity or through hole 457 adapted to matingly form an interference fit with the end of the core portion 454 (FIGS. 26-28) and a pair of through holes 472 which permit passage of electrical wires or leads connected to an electromagnet or magnetic coil 414 (FIGS. 37-39) of the prosthetic knee of the present invention.

In one preferred embodiment, and referring in particular to FIGS. 35 and 36, the core side plate 418 is dimensioned and configured such that the length $L_{351}$ is about 1.14 cm (0.448 inches), the length $L_{352}$ is about 1.05 cm (0.413 inches), the hole diameter $D_{355}$ is about 1.78 mm (0.070 inches) and the diameter $D_{363}$ is about 1.42 cm (0.560 inches). The other dimensions $D_{351}$, $D_{352}$, $D_{353}$, $D_{354}$, $\theta_{351}$, $D_{361}$, $D_{362}$, [$W_3$] $W_{361}$ and $W_{362}$ are substantially the same as the dimensions $D_{311}$, $D_{312}$, $D_{313}$, $D_{314}$, $\theta_{311}$, $D_{321}$, $D_{322}$, $W_{321}$ and $W_{322}$, respectively, as shown on FIGS. 31 and 32 and stated above for the first core side plate 416. In other preferred embodiments, the core side plate 418 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

FIGS. 37-39 show one preferred embodiment of an electromagnet, magnetic coil or wire spool 414 of a magnetorheologically actuated prosthetic knee of the present invention.

The magnetic coil 414 generally comprises a bobbin 340 having a pair of flanges 342, 344 at each end, winding 350 generally circumscribing the bobbin 340 and connected to electrical lead wires 352. A pair of slots or through holes 346, 348 in the bobbin flange 344 permit passage of the leads 352 which connect to a battery or other power source.

The magnetic coil 414 is preferably generally cylindrical in shape and has a generally cylindrical through passage 358 for receiving the core 412 (FIGS. 26-28) to mechanically connect the magnetic coil 414 to the core 412. The flanges 342 and 344 are received in grooves or recesses of respective side plates 416 and 418 (FIGS. 29-36) to mechanically connect the magnetic coil 414 to the side plates 416, 418. Thus, as the core side plates 416, 418 rotate so do the magnetic coil 414 and core 412.

Preferably, the bobbin 440 is fabricated from polyphenylene sulfide having a temperature rating of about 200° Celsius. The winding 350 preferably comprises three hundred and forty turns of 30 AWG copper wire having a resistance of about 8.03 ohms (Ω) and a power rating of about 13.7 watts at about 10.5 volts DC. The winding insulation comprises a suitable material having a temperature rating of about 155° Celsius. Preferably, the lead wires 352 comprise 24 AWG stranded wire about 8 inches long and covered with a teflon insulation with an about 0.25 inches section stripped and tinned.

In one preferred embodiment, and referring in particular to FIGS. 38 and 39, the electromagnet or magnetic coil 414 is dimensioned and configured such that the length $L_{381}$ is about 1.138 cm (0.448 inches), the length $L_{382}$ is about 1.05 cm (0.413 inches), the width $W_{381}$ is about 0.762 mm (0.030 inches), the radius of curvature $R_{381}$ is about 0.381 mm (0.015 inches), the diameter $D_{381}$ is about 0.762 mm (0.030 inches), the diameter $D_{391}$ is about 2.45 cm (0.965 inches), the diameter $D_{392}$ is about 1.89 cm (0.745 inches), the diameter $D_{393}$ is about 2.02 cm (0.795 inches), the length $L_{391}$ is about 1.95 cm (0.766 inches), the length $L_{392}$ is about 1.74 cm (0.686 inches), the length $L_{393}$ is about 1.02 mm (0.040 inches), the length $L_{394}$ is about 1.02 mm (0.040 inches) and the thickness $T_{391}$ is about 0.635 mm (0.025 inches). In other preferred embodiments, the magnetic coil 414 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

FIGS. 40-44 show one preferred embodiment of an inner spline 422 of a magnetorheologically actuated prosthetic knee of the present invention. The inner spline 422 comprises a plurality of longitudinal grooves or notches 484 for engaging or mating with corresponding teeth of rotors 420 (FIGS. 45-47) and a substantially central cavity 476 for receiving the magnetic coil 414 (FIGS. 37-39). Preferably, the inner spline 422 comprises nine substantially equally spaced grooves 484 having a substantially rectangular or square shape with rounded corners.

Figure 31:
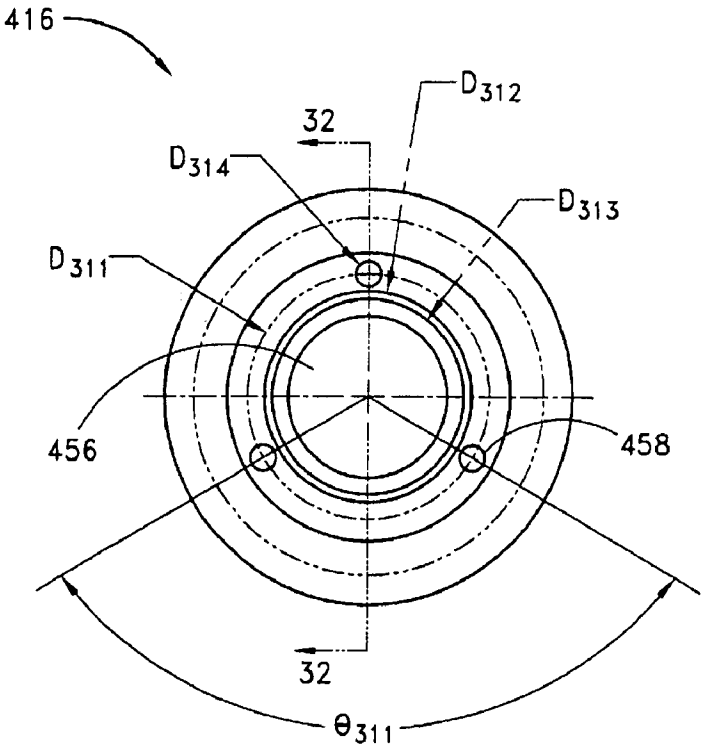
FIG. 31 is a rear view of the core side plate of FIG. 29.
Figure 33:
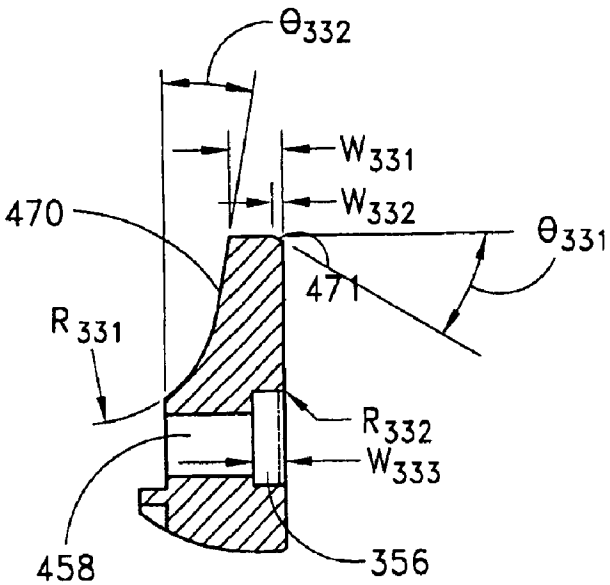
FIG. 33 is an enlarged view of region 33-33 of FIG. 32.
Figure 30:
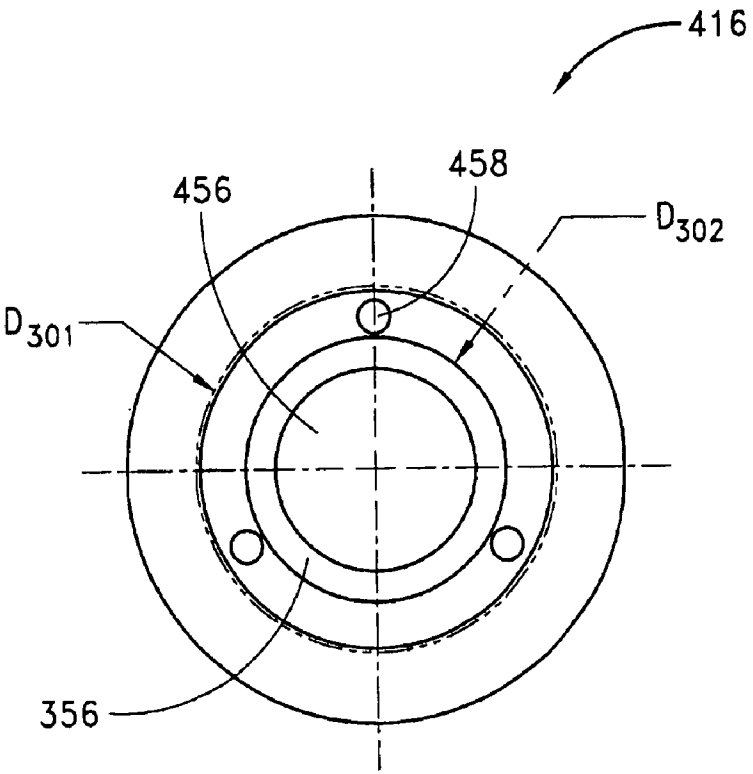
FIG. 30 is a front view of the core side plate of FIG. 29.

The inner spline cavity 476 preferably includes three longitudinal cavities or passages 478 which are substantially aligned with the bolt-receiving holes of the core side plates 416, 418 (FIGS. 31 and 35). The passages 478 receive bolts or the like to fasten or secure the inner spline 422 and the core side plates 416, 418. The inner spline cavity 476 further includes a plurality of longitudinal recesses 360 which serve to reduce the weight of the inner spline 422, and hence that of the prosthetic knee.

The inner spline 422 preferably comprises a flange 480 at each end to receive an O-ring, gasket or the like to form a static seal between the rotatable inner spline 422 and the rotatable core side plates 416, 418. An adjacent step, shoulder or flange 362 is also provided on each end to facilitate mounting of the O-rings or gaskets on the inner spline 422 during assembly of the prosthetic knee.

Preferably, the inner spline 422 is manufactured by wire electro-discharge machining (EDM). The inner spline 422 is preferably fabricated from titanium or a titanium alloy to provide a non-ferrous yet strong, hard surface with low weight to engage the rotors 420 and transmit torque from them. More preferably, the inner spline is fabricated from 6A1-4V titanium alloy.

In one preferred embodiment, and referring in particular to FIGS. 41-44, the inner spline 422 is dimensioned and configured such that the blind-circle diameter $D_{411}$ is about 2.85 cm (1.120 inches), the diameter $D_{412}$ is about 2.46 cm (0.970 inches), the passage diameter $D_{413}$ is about 2.95 mm (0.116 inches), the angle $\theta_{411}$ is typically about 120°, the angle $\theta_{412}$ is typically about 40°, the length $L_{421}$ is about 2.24 cm (0.881 inches), the length $L_{422}$ is about 1.96 cm (0.771 inches), the curved length $L_{431}$ is about 1.02 cm (0.402 inches), the curved length $L_{432}$ is about 4.17 mm (0.164 inches), the curved length $L_{433}$ is about 1.88 mm (0.074 inches), the curved length $L_{434}$ is about 8.92 mm (0.351 inches), the major diameter $D_{431}$ is about *3.63 cm* (1.430 inches), the diameter $D_{432}$ is about *3.43 cm* (1.350 inches), the diameter $D_{433}$ is about *2.90 cm* (1.140 inches), the profile tolerance width $W_{431}$ is about 0.0254 mm (0.001 inches), the radii of curvature $R_{431}$, $R_{432}$, $R_{433}$, $R_{434}$, $R_{435}$ are about 1.27 mm (0.050 inches), 1.27 mm (0.050 inches), 0.762 mm (0.030 inches), 0.381 mm (0.015 inches), 0.381 mm (0.015 inches), respectively, the angle $\theta_{431}$ is about 20°, the length $L_{441}$ is about (0.055 inches), the length $L_{442}$ is about 0.381 mm (0.015 inches), the length $L_{443}$ is about 0.127 mm (0.005 inches), the length $L_{444}$ is about 0.127 mm (0.005 inches), the diameter $D_{441}$ is about 3.345 cm (1.317 inches), the diameter $D_{442}$ is about 3.226 cm (1.270 inches), the radius of curvature $R_{441}$ is about 0.20 mm (0.008 inches) and the radius of curvature $R_{442}$ is about 0.51 mm (0.020 inches). In other preferred embodiments, the inner spline 422 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

Figure 41:
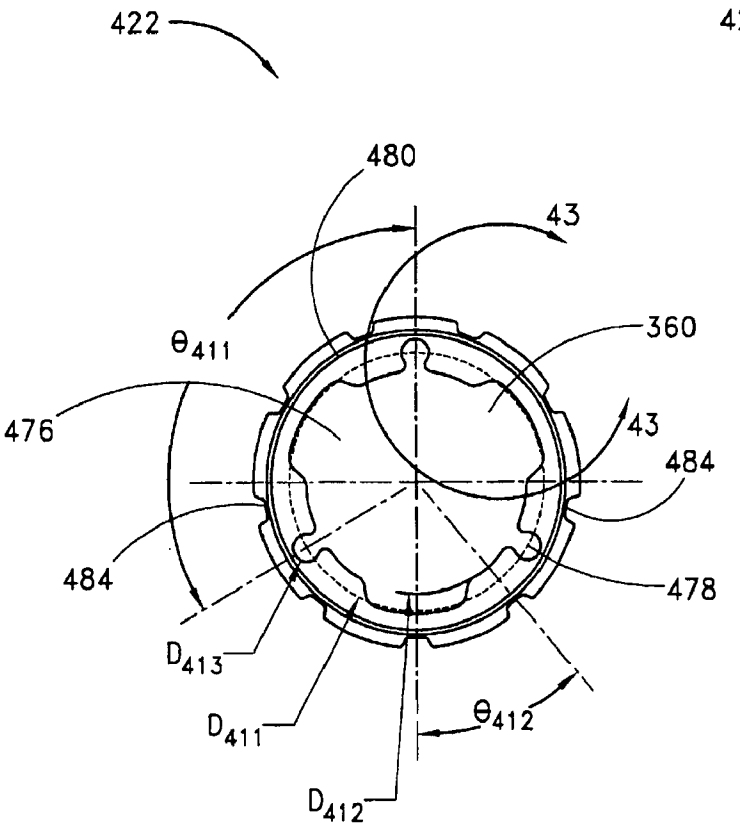
FIG. 41 is an end view of the inner spline of FIG. 40.
Figure 44:
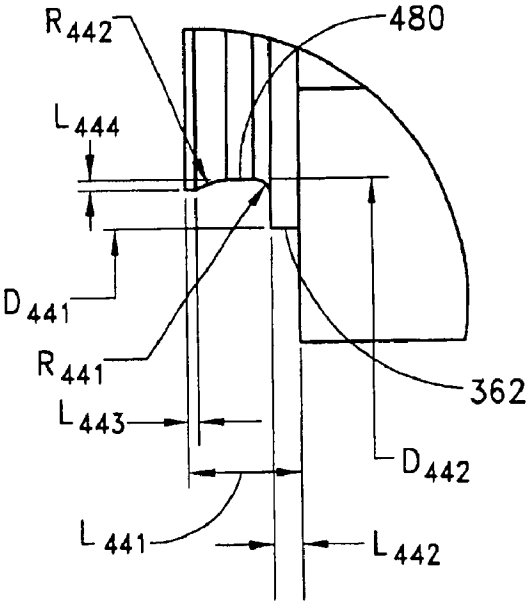
FIG. 44 is an enlarged view of region 44-44 of FIG. 42.
Figure 43:
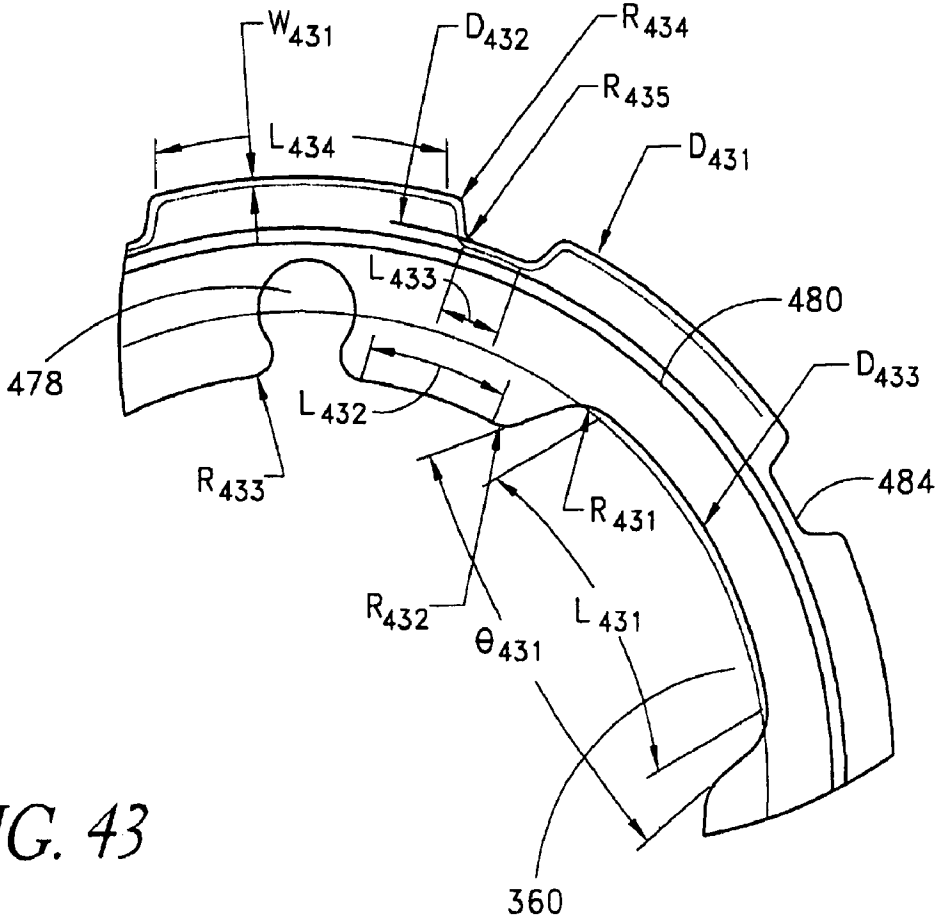
FIG. 43 is an enlarged view of region 43-43 of FIG. 41.
Figure 47:
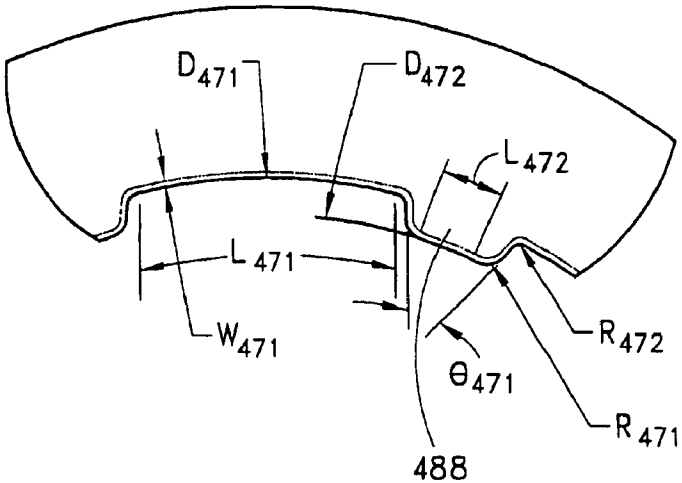
FIG. 47 is an enlarged view of region 47-47 of FIG. 45.
Figure 46:
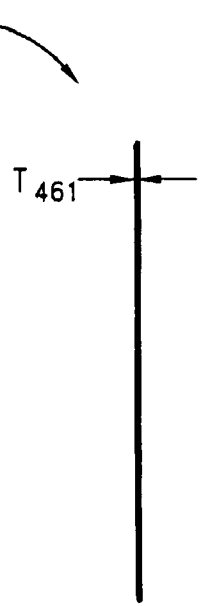
FIG. 46 is a side view of the rotor of FIG. 45.
Figure 45:
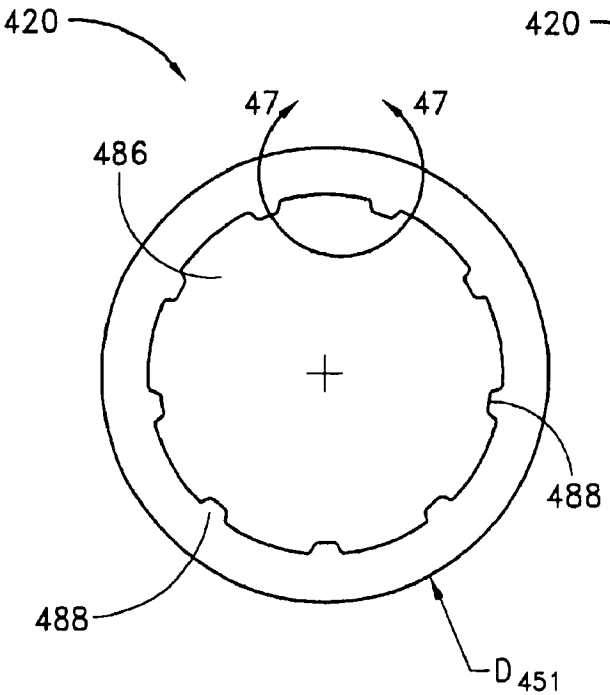
FIG. 45 is a front view of a rotor having features and advantages in accordance with one preferred embodiment of the present invention.

FIGS. 45-47 show one preferred embodiment of one of the rotors or inner blades 420 of a magnetorheologically actuated prosthetic knee of the present invention. The preferably annular or ring shaped thin rotor 420 is generally circular in shape and comprises a substantially central cavity or through hole 486 having a plurality of inwardly extending teeth 488 adapted to engage or mate with the inner spline grooves 484 (FIG. 41). Preferably, the rotor 420 comprises nine approximately equally spaced teeth 488 which are generally rectangular or square shaped with rounded corners.

The rotors 420 are preferably fabricated from a mechanically hard, magnetically soft material that has a high saturation flux density. More preferably, the rotors 420 are fabricated from blue temper steel. The rotors 420 are preferably formed by wire electro-discharge machining (EDM). Advantageously, this permits a high degree of manufacturing precision and avoids or mitigates any backlash, jarring or play between the rotors 420 and inner spline 422 which may otherwise cause discomfort to the patient.

In one preferred embodiment, and referring in particular to FIGS. 45-47, the rotors 420 are dimensioned and configured such that the major outer diameter $D_{451}$ is about 4.851 cm (1.910 inches), the thickness $T_{461}$ is about 0.203 mm (0.008 inches), the curved length $L_{471}$ is about 9.12 mm (0.359 inches), the curved length $L_{472}$ is about 1.73 mm (0.068 inches), the major inner diameter $D_{471}$ is about 3.642 cm (1.434 inches), the minor inner diameter $D_{472}$ is about 3.439 cm (1.354 inches), the profile tolerance width $W_{471}$ is about 0.0254 mm (0.001 inches), the radius of curvature $R_{471}$ is about 0.508 mm (0.020 inches), the radius of curvature $R_{472}$ is about 0.254 mm (0.010 inches) and the angle $\theta_{471}$ is about 40°. In other preferred embodiments, the rotors 420 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, the ratio between the rotor major outer diameter ($D_{451}$) and the rotor major inner diameter ($D_{471}$) is about 1.3. In another preferred embodiment, the ratio between the rotor major outer diameter ($D_{451}$) and the rotor major inner diameter ($D_{471}$) ranges between about 1.2 to about 5. In yet another preferred embodiment, the ratio between the rotor major outer diameter ($D_{451}$) and the rotor major inner diameter ($D_{471}$) ranges between about 1.1 to about 10. In other preferred embodiments, this ratio may be varied with efficacy, as required or desired, giving due consideration to the goals of providing a suitably compact, light weight and/or durable artificial knee, and/or of achieving one or more of the benefits and advantages as taught or suggested herein.

FIGS. 48-50 show one preferred embodiment of one of the stators or outer blades 430 of a magnetorheologically actuated prosthetic knee of the present invention. The preferably annular or ring shaped thin stator 430 is generally circular in shape and comprises a substantially central cavity or through hole 490 adapted to non-contactingly receive the inner spline 422 and a plurality of outwardly extending teeth 492 on the stator outer periphery which are adapted to engage or mate with grooves or notches on the interior of a rotatable outer spline of the prosthetic knee. Preferably, the stator 430 comprises nine approximately equally spaced teeth 492 which are generally rectangular or square shaped with rounded corners.

The stators 430 are preferably fabricated from a hard ferrous material that has a high saturation flux density. More preferably, the stators 430 are fabricated from blue temper steel. The stators 430 are preferably formed by wire electrodischarge machining (EDM). Advantageously, this permits a high degree of manufacturing precision and avoids or mitigates any backlash, jarring or play between the stators 430 and outer spline which may otherwise cause discomfort to the patient.

In one preferred embodiment, and referring in particular to FIGS. 48-50, the stators 430 are dimensioned and configured such that the major inner diameter $D_{481}$ is about 3.658 cm (1.440 inches), the thickness $T_{491}$ is about 0.203 mm (0.008 inches), the curved length $L_{501}$ is about 1.18 cm (0.464 inches), the curved length $L_{502}$ is about 3.66 mm (0.144 inches), the major outer diameter $D_{501}$ is about 5.07 cm (1.996 inches), the minor outer diameter $D_{502}$ is about 4.867 cm (1.916 inches), the profile tolerance width $W_{501}$ is about 0.0254 mm (0.001 inches), the radius of curvature $R_{501}$ is about 0.508 mm (0.020 inches), the radius of curvature $R_{502}$ is about 0.254 mm (0.010 inches) and the angle $\theta_{501}$ is about 20°. In other preferred embodiments, the stators 430 may be dimensioned and/or configured in alternate manners with efficacy, as required or desired, giving due consideration to the goals of providing a suitably compact, light weight and/or durable artificial knee, and/or of achieving one or more of the benefits and advantages as taught or suggested herein.

In one preferred embodiment, the ratio between the stator minor outer diameter ($D_{502}$) and the stator major inner diameter ($D_{481}$) is about 1.3. In another preferred embodiment, the ratio between the stator minor outer diameter ($D_{502}$) and the stator major inner diameter ($D_{481}$) ranges between about 1.2 to about 5. In yet another preferred embodiment, the ratio between the stator minor outer diameter ($D_{502}$) and the stator major inner diameter ($D_{481}$) ranges between about 1.1 to about 10. In other preferred embodiments, this ratio may be varied with efficacy, as required or desired, giving due consideration to the goals of providing a suitably compact, light weight and/or durable artificial knee, and/or of achieving one or more of the benefits and advantages as taught or suggested herein.

Figure 51:
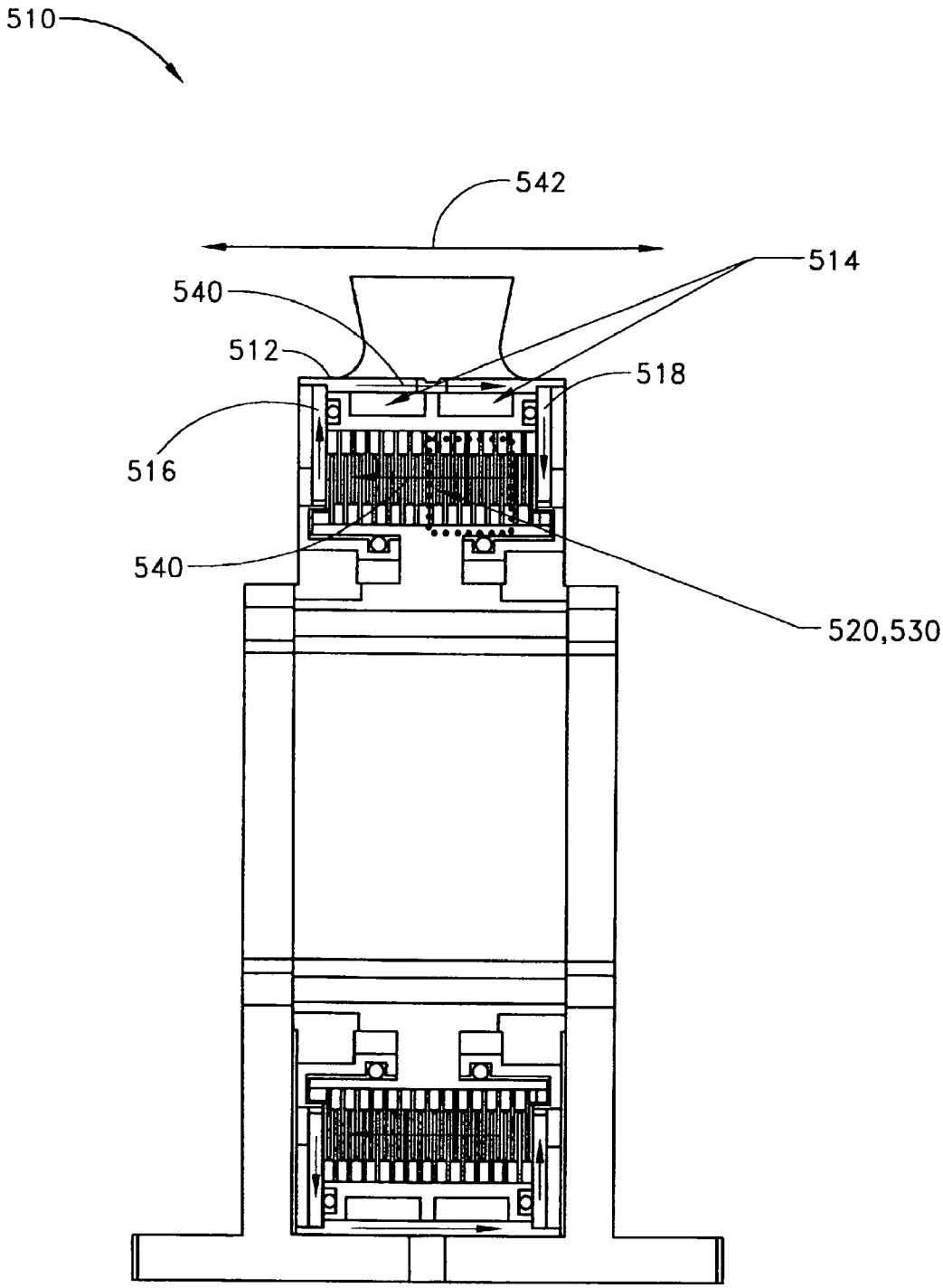
FIG. 51 is a schematic cross section view of another preferred embodiment of a magnetorheologically actuated prosthetic knee in which the magnetic return path passes through the exterior of the knee.

FIG. 51 shows a magnetorheologically actuated prosthetic knee 510 having features and advantages in accordance with another preferred embodiment of the present invention. In this embodiment, the magnetic return path passes through the exterior of the prosthetic knee 510. Such a configuration can allow for a more compact and/or light weight system design. Other suitable magnetic return paths can be selected or configured, as needed or desired, giving due consideration to the goals of achieving one or more of the benefits and advantages as taught or suggested herein.

Referring to FIG. 51, a magnetic field 540 is generated by the actuation of an electromagnet or magnetic coil 514 preferably positioned between a plurality of interspersed alternating rotors (inner blades) 520 and stators (outer blades) 530 and an outer magnetically soft housing or casing 512 of the prosthetic knee 510. The active portion of the magnetic field 540 passes (travelling substantially in the lateral direction 542) through the rotors 520, stators 530 and the magnetorheological fluid in the gaps therebetween. The return path of the magnetic field 540 passes radially outwards through a magnetically soft side plate 516, laterally through the knee exterior 512 and radially inwards through a second magnetically soft side plate 518.

While the components and techniques of the present invention have been described with a certain degree of particularity, it is manifest that many changes may be made in the specific designs, constructions and methodology hereinabove described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A prosthetic knee, comprising:

a plurality of rotors being rotatable about a longitudinal axis of said prosthetic knee;

a plurality of stators alternatingly interspersed with said rotors to form gaps therebetween;

a fluid adapted to undergo a rheology change in response to an applied magnetic field and residing in said gaps formed between said rotors and said stators;

whereby, controlled variation of said magnetic field varies the fluid rheology and shearing of said fluid caused by relative rotation between said rotors and stators during knee rotation generates a controllable variable knee torque.

2. The prosthetic knee of claim 1, wherein said stators are rotatable about the longitudinal axis of said prosthetic knee.

3. The prosthetic knee of claim 1, wherein *at* least one of said rotors and said stators are laterally displaceable about the longitudinal axis of said prosthetic knee to create mechanical contact between adjacent rotors and stators to provide a frictional component to the torque.

4. The prosthetic knee of claim 1, wherein said rotors and said stators comprise a magnetically soft material.

5. The prosthetic knee of claim 1, wherein said rotors and said stators comprise generally annular disks.

6. The prosthetic knee of claim 5, wherein said rotors and said stators have a thickness of about 0.2 mm (0.008 inches).

7. The prosthetic knee of claim 1, wherein said plurality of rotors comprises hundred or less rotors and said plurality of stators comprises hundred or less stators.

8. The prosthetic knee of claim 7, wherein said plurality of rotors comprises forty rotors and said plurality of stators comprises forty one stators.

9. The prosthetic knee of claim 1, wherein said gaps between said rotors and said stators have a size in the range from about 10 microns (μm) to about 100 microns (μm).

10. The prosthetic knee of claim 9, wherein said gaps between said rotors and said stators have a size of about 40 microns (μm).

11. The prosthetic knee of claim 1, wherein said rotors and said stators comprise generally cylindrical tubes.

12. The prosthetic knee of claim 1, wherein said rotors and said stators comprise blue temper steel or silicon steel.

13. The prosthetic knee of claim 1, wherein said fluid comprises a magnetically controllable medium.

14. The prosthetic knee of claim 1, wherein said fluid comprises a magnetorheological fluid adapted to undergo a viscosity change in response to variation in said magnetic field.

15. The prosthetic knee of claim 1, further comprising a magnet to generate said magnetic field which passes through said rotors, said stators and said fluid.

16. The prosthetic knee of claim 1, further comprising a generally central core in mechanical communication with a pair of side plates to form a magnetic return path for said magnetic field.

17. The prosthetic knee of claim 16, wherein said core and said side plates comprise an iron-cobalt (FeCo) high magnetic saturation alloy.

18. The prosthetic knee of claim 16, wherein at least one of said side plates is laterally displaceable about the longitudinal axis of said prosthetic knee.

19. The prosthetic knee of claim 1, further comprising:

a substantially central core and a pair of side plates formed from a magnetically soft material to create a magnetic return path; and an electromagnet positioned between said core and said rotors and said stators and being responsive to an electrical signal to generate said magnetic field to cause a controlled change in the rheology of said fluid.

20. The prosthetic knee of claim 1, further comprising a rotatable inner spline with said rotors engaged with said inner spline.

21. The prosthetic knee of claim 20, wherein said inner spline comprises a plurality of longitudinal grooves and each of said rotors comprises a plurality of teeth matingly engaged with said longitudinal grooves of said inner spline.

22. The prosthetic knee of claim 20, wherein said inner spline comprises a titanium alloy.

23. The prosthetic knee of claim 20, further comprising a pair of bearings in rotary communication with said inner spline.

24. The prosthetic knee of claim 23, further comprising a pair of rotatable side mounting forks with each in mechanical communication with one of said bearings to facilitate connection of said prosthetic knee to a prosthetic shin.

25. The prosthetic knee of claim 1, further comprising an outer spline with said stators engaged with said outer spline.

26. The prosthetic knee of claim 25, wherein said outer spline comprises a plurality of longitudinal grooves and each of said stators comprises a plurality of teeth matingly engaged with said longitudinal grooves of said outer spline.

27. The prosthetic knee of claim 25, wherein said outer spline comprises an anodized aluminum alloy.

28. The prosthetic knee of claim 25, wherein said outer spline comprises a pyramid stub to facilitate connection of said prosthetic knee to a residual limb socket.

29. The prosthetic knee of claim 1, further comprising a magnetic exterior portion and a pair of mechanically connected magnetic side plates to create a magnetic return path for said magnetic field.

30. The prosthetic knee of claim 1, further comprising a cushioned flexion stop system to control the maximum flexion of said prosthetic knee.

31. The prosthetic knee of claim 1, further comprising a cushioned extension stop system to control the maximum extension of said prosthetic knee.

32. The prosthetic knee of claim 1, further comprising an extension assist device for facilitating in extending said prosthetic knee.

33. The prosthetic knee of claim 1, further comprising a controller to control and monitor the actuations of said prosthetic knee.

34. A prosthetic assembly, comprising:

the prosthetic knee as recited in claim 1;

a stump socket in mechanical communication with said prosthetic knee and adapted to receive the residual limb of an amputee;

a prosthetic shin portion in mechanical communication with said prosthetic knee; and a prosthetic foot in mechanical communication with said prosthetic shin portion.

*35. A prosthetic device, comprising:*

*at least one rotor being actuatable about an axis of the device;*

*at least one stator being spaced from said at least one rotor and forming a gap therebetween; and*

*a fluid adapted to undergo a rheology change in response to an applied magnetic field and residing in said gap;*

*wherein controlled variation of said magnetic field varies the fluid rheology, and shearing of said fluid caused by relative rotation between said at least one rotor and said at least one stator during device rotation generates a controllable variable torque; and*

*wherein said prosthetic device comprises a prosthetic joint.*

*36. The prosthetic device of claim 35, wherein said at least one rotor is generally cylindrical.*

*37. The prosthetic device of claim 35, wherein said at least one stator is generally cylindrical.*

*38. The prosthetic device of claim 35, wherein said at least one rotor and said at least one stator are generally cylindrical.*

*39. The prosthetic device of claim 35, further comprising an outer housing.*

*40. The prosthetic device of claim 39, wherein said outer housing includes a connector for facilitating connection to a stump socket or a residual limb of an amputee.*

*41. The prosthetic device of claim 40, wherein said connector is a pyramid connector.*

*42. The prosthetic device of claim 35, wherein the joint is a prosthetic knee.*

*43. The prosthetic device of claim 35, wherein said fluid comprises a magnetorheological fluid.*

*44. The prosthetic device of claim 35, further comprising at least one sensor for measuring an angle of rotation between said at least one rotor and said at least one stator.*

*45. The prosthetic device of claim 35, further comprising a microprocessor.*

*46. The prosthetic device of claim 35, in combination with a prosthetic foot mechanically coupled to the joint.*

*47. A prosthetic device system, comprising:*

*an outer generally cylindrical member comprising a substantially cylindrical cavity;*

*an inner generally cylindrical member provided within said substantially cylindrical cavity, wherein said inner and outer generally cylindrical members are rotatable about a device axis of rotation relative to one another;*

*a magnetorheological fluid residing in a cavity between said inner and outer generally cylindrical members; and*

*a connector at a top end of said outer generally cylindrical member for facilitating connection to a stump socket or a residual limb of an amputee;*

*wherein a damping torque to control device rotation is provided by shearing of said magnetorheological fluid; and*

*wherein said prosthetic device system comprises a prosthetic joint system.*

*48. The prosthetic device system of claim 47, wherein said connector is a pyramid connector.*

*49. The prosthetic device system of claim 47, wherein said inner generally cylindrical member is rotatable about a knee joint axis of rotation relative to said outer generally cylindrical member.*

*50. The prosthetic device system of claim 47, wherein said inner generally cylindrical member is mechanically connected to a prosthetic foot.*

*51. The prosthetic device system of claim 47, further comprising side walls for enclosing said magnetorheological fluid.*

*52. The prosthetic device system of claim 47, further comprising an electromagnet for applying a magnetic field to said magnetorheological fluid.*

*53. The prosthetic device system of claim 52, wherein said electromagnet is coupled to one of said generally cylindrical members.*

*54. The prosthetic device system of claim 52, further comprising a power source connected with said electromagnet.*

*55. The prosthetic device system of claim 47, further comprising a feedback control system to control and monitor actuations of the prosthetic joint system.*

*56. The prosthetic device system of claim 47, further comprising at least one sensor for measuring an angle of rotation between said inner and outer generally cylindrical members.*

*57. The prosthetic device system of claim 47, further comprising a microprocessor and one or more sensors to provide control and monitor actuations of the prosthetic joint system.*

*58. The prosthetic device system of claim 47, wherein said magnetorheological fluid is sheared between adjacent cylinders.*

*59. A device to be worn by a wearer at a joint location, comprising:*

*a first surface;*

*a second surface spaced from said first surface to form a gap therebetween;*

*a fluid adapted to undergo a rheology change in response to an applied magnetic field and residing in said gap;*

*at least one of said first surface and said second surface being movable relative to the other;*

*wherein, variation of said field varies the rheology of said fluid and shearing of said fluid caused by relative motion between said first and second surfaces generates a controllable variable damping of the device; and*

*wherein the device comprises a prosthetic device, and wherein said prosthetic device comprises a prosthetic joint.*

*60. The device of claim 59, wherein said prosthetic joint comprises a prosthetic knee.*

*61. The device of claim 59, wherein said fluid comprises a magnetorheological fluid.*

*62. The device of claim 59, wherein said fluid comprises a magnetically controllable medium.*

*63. The device of claim 59, wherein said first and second surfaces are generally cylindrical.*

*64. The device of claim 59, wherein said field varies the viscosity of said fluid.*

* * * * *

UNITED STATES PATENT AND TRADEMARK OFFICE

CERTIFICATE OF CORRECTION

PATENT NO. : RE42,903 E
APPLICATION NO. : 11/490508
DATED : November 8, 2011
INVENTOR(S) : Bruce W. Deffenbaugh et al.

It is certified that error appears in the above-identified patent and that said Letters Patent is hereby corrected as shown below:

In the Specifications

In Column 1, Line 9, please insert the following:

--Notice: More than one reissue application has been filed for the reissue of U.S. Patent No. 6,764,520 B2. The reissue applications include U.S. Patent Application No. 11/490,508, filed July 20, 2006 (the present, now issued, application) and U.S. Patent Application No. 13/273,081, filed October 13, 2011, which is a continuation of the present, now issued, application.--.

In Column 6, Line 46, please change "and-having" to --and having--.

In Column 16, Line 34, please change "Currents." to --currents.--.

In Column 23, Line 41, please change "$\theta^{232}$" to --$\theta_{232}$--.

Signed and Sealed this
Twenty-ninth Day of April, 2014

Michelle K. Lee

Michelle K. Lee
*Deputy Director of the United States Patent and Trademark Office*